US 10,851,641 B2

(12) United States Patent
Yang et al.

(10) Patent No.: US 10,851,641 B2
(45) Date of Patent: Dec. 1, 2020

(54) ACOUSTIC TESTING OF CORE SAMPLES

(71) Applicant: Saudi Arabian Oil Company, Dhahran (SA)

(72) Inventors: Yunlai Yang, Dhahran (SA); Maher I. Almarhoon, Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 219 days.

(21) Appl. No.: 16/122,625

(22) Filed: Sep. 5, 2018

(65) Prior Publication Data

US 2020/0072039 A1    Mar. 5, 2020

(51) Int. Cl.
| | | |
|---|---|---|
| *E21B 47/02* | (2006.01) | |
| *E21B 47/0224* | (2012.01) | |
| *E21B 47/06* | (2012.01) | |
| *E21B 47/18* | (2012.01) | |
| *E21B 49/08* | (2006.01) | |
| *E21B 49/10* | (2006.01) | |

(52) U.S. Cl.
CPC .......... *E21B 47/0224* (2020.05); *E21B 47/06* (2013.01); *E21B 47/18* (2013.01); *E21B 49/081* (2013.01); *E21B 49/10* (2013.01)

(58) Field of Classification Search
CPC ..... G01N 2291/011; G01N 2291/0232; G01N 2291/0289; G01N 2291/105; G01N 29/07; G01N 29/223; G01N 29/227; G01N 33/24; G01N 3/00; E21B 47/0224; E21B 47/06; E21B 47/18; E21B 49/081; E21B 49/10
See application file for complete search history.

(56) References Cited

U.S. PATENT DOCUMENTS

| | | |
|---|---|---|
| 4,380,930 A | 4/1983 | Podhrasky et al. |
| 4,625,555 A | 12/1986 | Fujii |
| | (Continued) | |

FOREIGN PATENT DOCUMENTS

| | | |
|---|---|---|
| EP | 117280 | 4/1990 |
| EP | 294158 | 12/1993 |
| | (Continued) | |

OTHER PUBLICATIONS

International Search Report and Written Opinion issued in International Application No. PCT/US2019/049288 dated Nov. 21, 2019, 16 pages.

(Continued)

*Primary Examiner* — Francis C Gray
(74) *Attorney, Agent, or Firm* — Fish & Richardson P.C.

(57) ABSTRACT

A central member defines a sample chamber and includes an elastic material configured to enclose at least a portion of a sample, acoustic sensors configured to detect sound waves in the sample chamber, and acoustic emitters configured to emit sounds waves in the central member. A pressure-retaining case is configured to contain a pressurized fluid between an annulus formed between the pressure-retaining case and the central member. A switch is configured to connect or disconnect a pulser and receiver circuit to a specified emitter of the acoustic emitters. A data acquisition unit is configured to receive a signal from each of the acoustic sensors. A pulser and receiver circuit is configured to send an electric pulse to an acoustic emitter and a control signal to the data acquisition unit.

20 Claims, 14 Drawing Sheets

(56) References Cited

U.S. PATENT DOCUMENTS

| | | | |
|---|---|---|---|
| 5,176,631 A * | 1/1993 | Koenig | A61M 5/365 |
| | | | 128/DIG. 13 |
| 5,178,005 A * | 1/1993 | Peterson | G01N 29/07 |
| | | | 73/152.11 |
| 5,243,855 A | 9/1993 | Steiger et al. | |
| 5,265,461 A | 11/1993 | Steiger et al. | |
| 5,678,643 A | 10/1997 | Robbins et al. | |
| 5,691,475 A | 11/1997 | Marsala | |
| 5,753,812 A | 5/1998 | Aron et al. | |
| 5,868,030 A | 2/1999 | Brumley et al. | |
| 6,382,332 B1 | 5/2002 | Eaton | |
| 6,988,566 B2 | 1/2006 | Lockerd, Sr. et al. | |
| 7,289,909 B2 | 10/2007 | Thomamnn et al. | |
| 7,404,456 B2 | 7/2008 | Weaver et al. | |
| 7,823,451 B2 | 11/2010 | San | |
| 9,568,629 B2 | 2/2017 | Almarhoon | |
| 2011/0266058 A1 | 11/2011 | Kumar et al. | |
| 2013/0075160 A1 | 3/2013 | Yang | |
| 2013/0080060 A1 | 3/2013 | Yang | |
| 2013/0080065 A1 | 3/2013 | Yang | |
| 2017/0276649 A1 * | 9/2017 | Schmitz | G01N 29/043 |

FOREIGN PATENT DOCUMENTS

| | | | |
|---|---|---|---|
| EP | 2930507 A1 * | 10/2015 | |
| WO | WO-03027663 A1 * | 4/2003 | |
| WO | 2013049014 | 4/2013 | |
| WO | 2013049111 | 4/2013 | |
| WO | 2013049140 | 4/2013 | |

OTHER PUBLICATIONS

Masood et al.; "A Critical Review on Estimation of Rock Properties Using Sound Levels Produced during Rotary Drilling"; International Journal of Earth Sciences and Engineering; Dec. 2012; pp. 1809-1814.

Rector III et al.; "Radiation Pattern and Seismic Waves Generated by a Working Roller-Cone Drill.Bit"; Geophysics; Society of Exploration Geophysicists; vol. 57, No. 10; Oct. 1992; pp. 1319-1333.

Soma, Nobukazu et al.; "Trial of Coal Seam Imaging by Cross Correlation Analysis of Drilling Noise at Open-Pit Mine Based on Single Point 3C Downhole Observation"; Proceedings of the 11th SEGJ International Symposium; Yokohama, Japan; Nov. 18-21, 2013; pp. 302-306.

Zborovjan, Martin et al.; "Acoustic Identification of Rocks during Drilling Process"; Acta Montanistica Slovaca; Dec. 1, 2003; pp. 191-193.

corelab.com' [online], "Advanced Rock Properties: Acoustic Velocity System, AVMS-350HT," available on or before Jun. 18, 2017, [retrieved on May 22, 2018], retrieved from URL: <http://www.corelab.com/cli/advanced-rock-properties/acoustic-velocity-system>, 2 pages.

Johnson, "Design and Testing of a Laboratory Ultrasonic Data Acquisition System for Tomography," thesis for degree of Master of Science in Mining and Minerals Engineering, Virginia Polytechnic Institute and State University, Dec. 2, 2004, 108 pages.

Gemmeke and Ruiter, "3D Ultrasound computer tomography for medical imaging," Nuclear Instruments and Methods in Physics Research A, vol. 580, Issue 2, Oct. 1, 2007, 9 pages.

Ruiter et al., "3D ultrasound computer tomography of the breast: A new era?" European Journal of Radiology 81S1, Sep. 2012, S133-S134, 11 pages.

International Search Report and Written Opinion of the International Searching Authority issued in International Application No. PCT/US2015/053405 dated Jan. 25, 2016; 12 pages.

Gulf Cooperation Council issued in GCC Application No. GC 2015-30118 on Feb. 22, 2018, 3 pages.

Gulf Cooperation Council issued in GCC Application No. GC 2015-30118 on Jul. 9, 2018, 3 pages.

GCC Examination Report in GCC Appln. No. GC 2019-38245, dated May 31, 2020, 3 pages.

* cited by examiner

ACOUSTIC TESTING OF CORE SAMPLES

TECHNICAL FIELD

This disclosure relates to testing of core samples obtained from wellbores.

BACKGROUND

Acoustic properties of a solid material, such as acoustic velocity of rocks, are important parameters in different applications and geoscientific research, for example, in seismic data processing, in assessment of physical properties of materials, and other similar fields.

A conventional triaxial test apparatus used to measure mechanical properties of a rock sample under different stress conditions is normally used for measuring acoustic properties of rock samples. With such an apparatus, a test is performed inside a pressure cell. A rock sample is sealed within an elastic impermeable membrane and then placed between a bottom end cap and a top end cap. A confining pressure is applied to the sample. Pore pressure and back pressure are also applied to maintain a pore pressure gradient through the sample. Then an axial load is applied to the top end cap to generate a shear stress. Throughout the test, mechanical properties, such as permeability, stress/strain relationship, and shear strength can be derived.

SUMMARY

This specification describes technologies relating to acoustic testing of core samples.

An example implementation of the subject matter described within this disclosure is a testing apparatus with the following features. A central member defines a sample chamber and includes an elastic material configured to enclose at least a portion of a sample, acoustic receivers configured to detect sound waves in the sample chamber, and acoustic transmitters configured to emit sounds waves in the central member. A pressure-retaining case surrounds a radial surface of the central member. The pressure-retaining case is configured to contain a pressurized fluid between an annulus formed between the pressure-retaining case and the central member.

Aspects of the example implementation, which can be combined with the example implementation alone or in combination, include the following. The acoustic transmitters are ultrasonic emitters and the acoustic receivers are ultrasonic acoustic sensors.

Aspects of the example implementation, which can be combined with the example implementation alone or in combination, include the following. The pressure-retaining case includes a case central member with an upper portion and a lower portion connected to the upper portion along a first edge of the upper portion and a first edge of the lower portion by a hinge. A second edge of the upper portion and a second edge of the lower portion are configured to abut one another when the case central member is in a closed position. The upper portion and the lower portion defining a first open end of the pressure-retaining case and a second open end of the pressure-retaining case when in the closed position. A right-side member is configured to seal the pressure retaining case and the central member. The right-side member is configured to seal the first open end of the pressure-retaining case. A left-side member is configured to seal the pressure-retaining case and the central member. The left-side member is configured to seal the second open end of the pressure-retaining case that is opposite of the first open end of the pressure retaining case.

Aspects of the example implementation, which can be combined with the example implementation alone or in combination, include the following. The left-side member and the right side member are secured with one or more lock mechanisms.

Aspects of the example implementation, which can be combined with the example implementation alone or in combination, include the following. The acoustic receivers and acoustic transmitters are arranged so that one sensor or one emitter is positioned substantially every 30° around a central longitudinal axis of the sample chamber.

Aspects of the example implementation, which can be combined with the example implementation alone or in combination, include the following. There are two acoustic receivers for every one transmitter.

Aspects of the example implementation, which can be combined with the example implementation alone or in combination, include the following. The acoustic transmitters and acoustic receivers are arranged in rows transverse to a longitudinal axis of the sample chamber. A composition of each of the rows alternates between two receivers and one transmitter.

Aspects of the example implementation, which can be combined with the example implementation alone or in combination, include the following. At least one of the acoustic transmitters is oriented at an angle from an inner surface of the central member.

Aspects of the example implementation, which can be combined with the example implementation alone or in combination, include the following. A control system includes a switch coupled to each of the acoustic transmitters. The switch is configured to connect or disconnect a pulser and receiver to a specified transmitter of the acoustic transmitters. A data acquisition unit is coupled to each of the acoustic receivers. The data acquisition unit is configured to receive a signal from each of the acoustic receivers. A pulser and receiver circuit is coupled to the switch and the data acquisition unit. The pulser and receiver circuit is configured to send an electric pulse to one of the acoustic transmitters through the switch and send a control signal to the data acquisition unit.

Aspects of the example implementation, which can be combined with the example implementation alone or in combination, include the following. A pressure pump is coupled to the annulus between the central member and the pressure-retaining case. The pressure pump is configured to pressurize the annulus with fluid. A pressure sensor is coupled to the annulus between the central member and the pressure retaining case. The pressure sensor is configured to detect a pressure within the annulus.

An example implementation of the subject matter described within this disclosure is a method with the following features. A pressure containing member is pressurized to exert a uniform pressure on a sample. An acoustic pulse is emitted with one of several acoustic transmitters. The emitted acoustic pulse is received with one or more acoustic receivers.

Aspects of the example method, which can be combined with the example method alone or in combination, include the following. The acoustic emitters and the acoustic sensors are uniformly pressed against a surface of the sample by the elastic material and the pressure in the pressure containing member.

Aspects of the example method, which can be combined with the example method alone or in combination, include the following. The pressure containing member is depressurized. The acoustic emitters and the acoustic sensors are released from the surface of the sample in response to depressurizing the pressure containing member.

Aspects of the example method, which can be combined with the example method alone or in combination, include the following. Receiving the emitted acoustic pulse includes receiving a direct incident acoustic pulse through a sample. A reflected acoustic pulse is received through the sample.

Aspects of the example method, which can be combined with the example method alone or in combination, include the following. The received acoustic pulses are analyzed.

Aspects of the example method, which can be combined with the example method alone or in combination, include the following. A rock property is determined based on the received acoustic pulse.

Aspects of the example method, which can be combined with the example method alone or in combination, include the following. The determined rock property includes an acoustic velocity.

Aspects of the example method, which can be combined with the example method alone or in combination, include the following. Emitting an acoustic pulse includes sending a control signal to a switch from a computer to instruct the switch to make a connection between a pulser and receiver circuit and one of plurality of acoustic emitters. An electric pulse is sent to a specified acoustic emitter through the switch, from the pulser and receiver circuit, in response to the control signal being received by the switch.

Aspects of the example method, which can be combined with the example method alone or in combination, include the following. Receiving the emitted acoustic pulse includes sending a control signal to a data acquisition unit from a pulser and receiver circuit. A signal is received from one or more specified acoustic receivers in response to the control signal being received by the data acquisition unit.

An example implementation of the subject matter described within this disclosure is a system with the following features. A central member defines a sample chamber and includes an elastic material configured to enclose at least a portion of a sample, acoustic sensors configured to detect sound waves in the sample chamber, and acoustic emitters configured to emit sounds waves in the central member. A pressure-retaining case surrounds a radial surface of the central member. The pressure-retaining case is configured to contain a pressurized fluid between an annulus formed between the pressure-retaining case and the central member. A switch is coupled to each of the plurality of acoustic emitters. The switch is configured to connect or disconnect a pulser and receiver to a specified emitter of the acoustic emitters. A data acquisition unit is coupled to each of the acoustic sensors. The data acquisition unit is configured to receive a signal from each of the acoustic sensors. A pulser and receiver circuit is coupled to the switch and the data acquisition unit. The pulser and receiver circuit is configured to send an electric pulse to one of the plurality of acoustic emitters through the switch and to send a control signal to the data acquisition unit simultaneously. A pressure pump is coupled to the annulus between the central member and the pressure retaining case. The pressure pump is configured to pressurize the annulus with fluid. A pressure sensor is coupled to the annulus between the central member and the pressure-retaining case. The pressure sensor is configured to detect a pressure within the annulus.

Aspects of the example system, which can be combined with the example implementation alone or in combination, include the following. The plurality acoustic sensors and the plurality of acoustic transmitters are configured to be transverse to a received sample.

Aspects of the example system, which can be combined with the example implementation alone or in combination, include the following. A computer readable memory contains instructions including sending a first control signal to the switch to make a connection between the pulser and receiver circuit and one of the acoustic emitters. A computer readable memory contains instructions including sending a second control signal to the pulser and receiver circuit to command the pulser and receiver to send an electric pulse to a specified acoustic emitter through the switch and to send a control signal to the data acquisition unit simultaneously in response to the first control signal being received by the switch. A computer readable memory contains instructions including receiving a signal from one or more specified acoustic sensors through the data acquisition unit in response to the control signal being received by the data acquisition unit.

Particular implementations of the subject matter described in this specification can be implemented so as to realize one or more of the following advantages. Transducers are automatically and easily attached to the sample. The attachment is firm and stable to ensure a maximum transmission of signals between the transducers and the sample (good coupling). The attachment of the transducers is consistent among all transducers in one test, that is, all the transducers are attached to the sample under a same condition. The attachment of the transducers is also consistent among different test runs since the same pressing pressure can be applied to the transducers among the different runs. The loading and unloading of a sample is very easy and quick. The apparatus can handle a large and heavy sample, such as a one-meter-long rock core. Since a sample needs no adaptation and no contact with a coupling fluid, a test imposes minimum disturbance to the sample.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Some large core samples do not fit within a triaxial or uniaxial test apparatus, nor can they fit in a 3D ultrasound computer tomography system for medical imaging. For example, a core that measures 3 feet by length and 2.5 inches by diameter is too large for conventional imaging systems. Cores extracted from oil well drilling or other types of borehole drilling are typically 3 feet long and several inches in diameter. Pores in a core sample can contain hydrocarbons and formation waters. During certain tests, such as. 3D ultrasound computer tomography system for medical imaging, a coupling fluid is used to couple sensor equipment and the testing object. If water is used as a coupling liquid in tests, liquids in the core may exchange with the coupling water. In these instances, the chemical and physical properties of the rock core may be affected by the water. Mounting ultrasonic transducers directly on the surface of a core sample by using an adhesive may damage the core. In addition, manually attaching and removing the transducers is very time consuming. To assist in real-time decision making, core properties of the rock core should be determined as soon as possible after the rock core is extracted. For example, testing a core sample on-site within one to two weeks would be ideal. Between extraction of the core and testing of the core, the core is kept in a sealed container with careful temperature control. A core that is properly stored can maintain its properties for up to two months between extraction and testing. During each measurement and between different measurements, transducers should be in effective and consistent contact with the sample. An apparatus that can quickly measure acoustic properties of a fresh large core in its virgin condition, with no, minimum, or otherwise reduced disturbance, with consistent attachment of transducers, and with easy operation does not currently exist.

The subject matter described herein discusses such a system. The system includes a sample chamber configured to confine a sample and transducers with a constant pressure and place ultrasonic transducers to the sample in a stable and consistent manner. The system also includes electronics and software to perform the desired tests. In addition, the system includes a pressurization system to exert a desired pressure on the sample and the transducers during testing.

Figure 1:
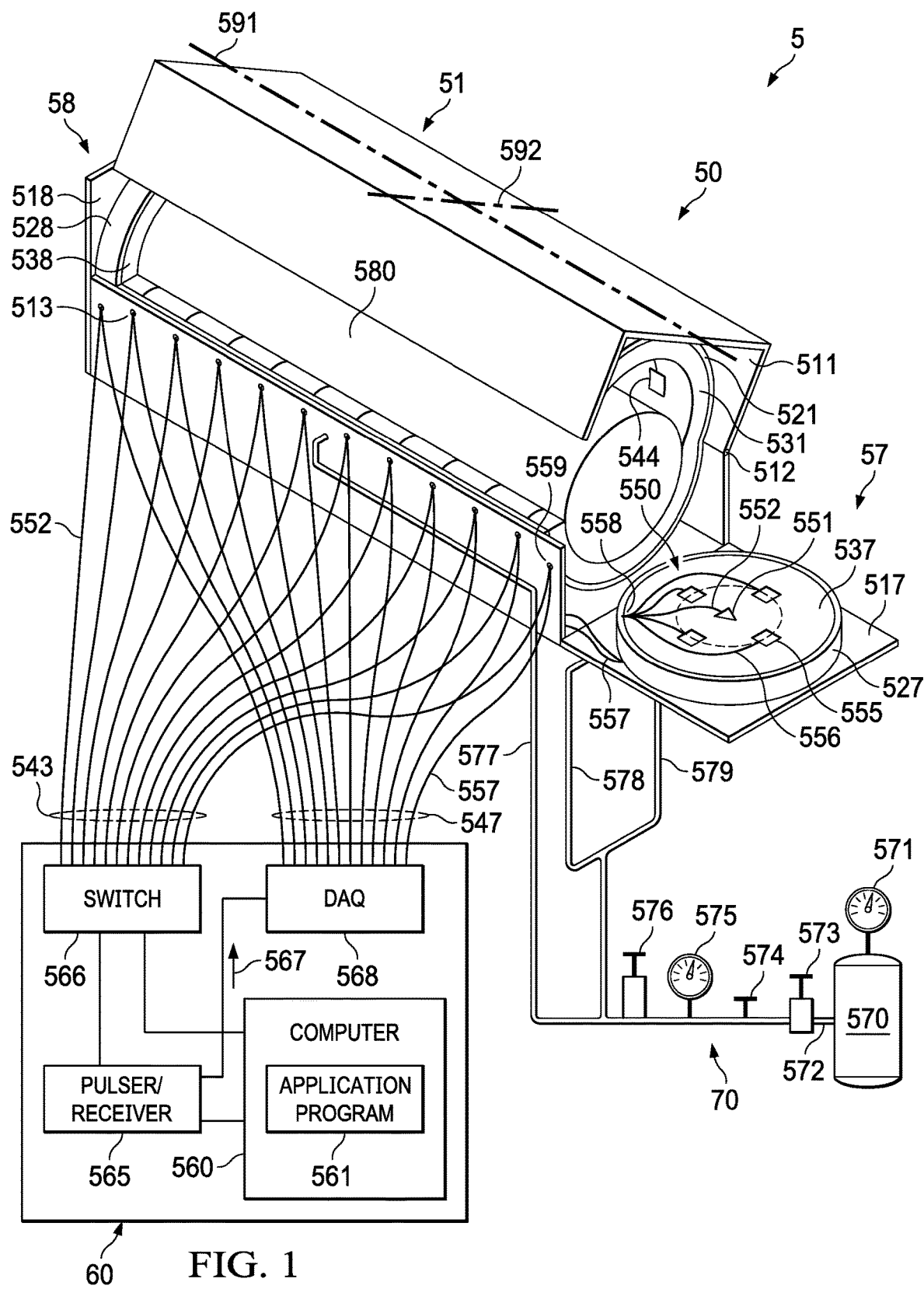
FIG. 1 is a schematic diagram of an example core testing system.
Figure 2:
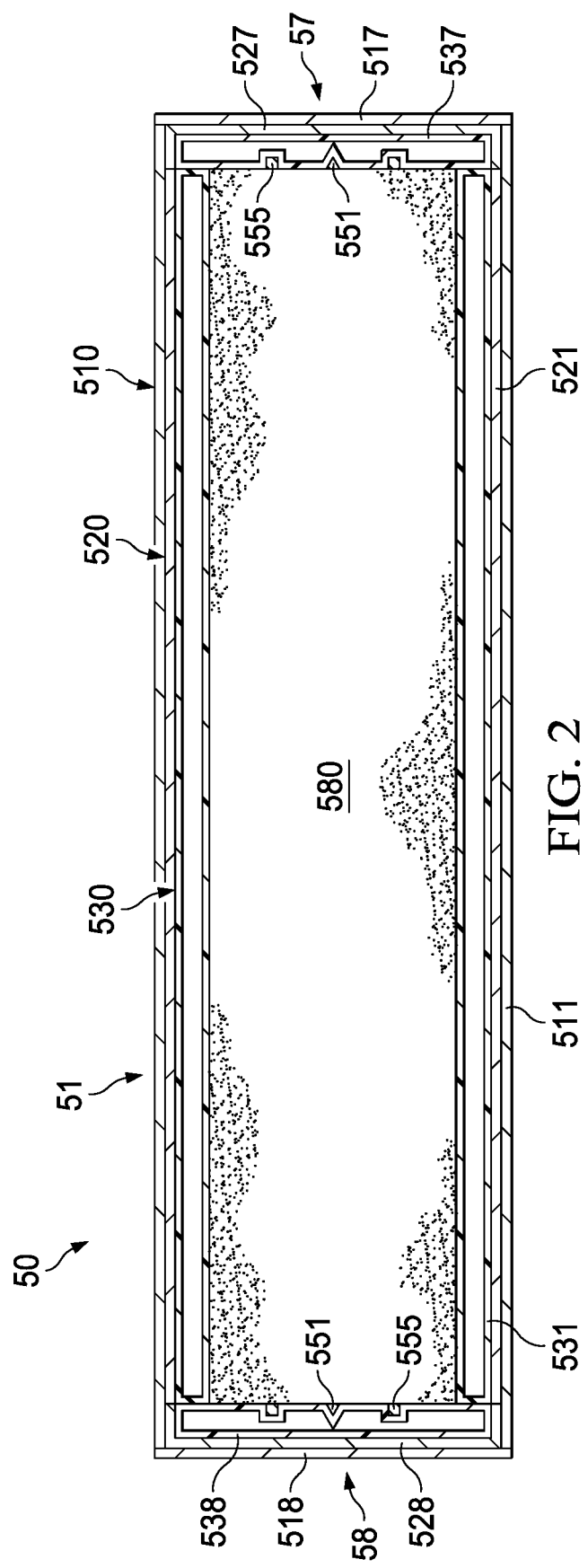
FIG. 2 is a schematic diagram showing a side cross-sectional view of a sample within a sample chamber.

FIG. 1 is a schematic diagram of an example core testing system 5 While FIG. 2 is a longitudinal cross-sectional view of the sample chamber 50 along a line 591 when the sample chamber 50 is closed. The following description refers to FIGS. 1-2. The system 5 includes a sample chamber 50 that has four major components: a housing 510 configured to retain and support a set of internal components, a rigid confining case 520 surrounded and supported by the housing 510 and provides rigidity with which to support a sample, a pressure jacket 530 that is fitted to and confined by the rigid confining case 520 and is configured to further support and surround a sample 580, and a set of ultrasonic transducers 544 entrained or otherwise supported along an inner surface of the pressure jacket 530. Further details about how the housing 510, the rigid confining case 520, and the pressure jacket 530 interact with one another is explained in greater detail later within this disclosure. A sample chamber 50 includes a center chamber member 51, right chamber member 57 positioned on a first side of the center chamber member 51, and left chamber member 58 positioned on a second side of the center chamber member 51. The second side of the center chamber member 51 is opposite the first side of the center chamber member 51. In the illustrated example, the left chamber member 57 and the right chamber member 58 are symmetric.

In the illustrated implementation, the housing 510 has a square cross-section while in a closed position, but may have other cross sections without departing from the scope of the disclosure. The housing 510 retains and supports several components contained within the housing 510 that will be discussed in greater detail later within this disclosure. The housing 510 has a center housing member 511, a right housing member 517 positioned on a first side of the central housing member 511, and a left housing member 518 positioned on a second side of the central housing member 511. The first side of the central housing member 511 and the second side of the central housing member 511 are opposite one another. The right housing member 517 and left housing member 518 are identical and are sized to match the outer cross section of the center housing member 511 in the illustrated example. The center housing member 511 has an identical upper part and lower part, joined by a hinge 512 in the illustrated example. The center housing member 511 can be opened and closed along the hinge 512. In some instances, both the right housing member 517 and left housing member 518 are attached to the bottom side of the lower part of the center housing member 511 by a hinge (not shown). In some instances, the right housing member 517 and the left housing member 518 can be fully detachable from the center housing member 511. This arrangement allows the housing 510 being opened and closed in all directions and can make the loading and unloading of a large and heavy sample an easy operation. While the illustrated implementation is described with a hinge, other connection mechanisms can be used without departing from the scope of this disclosure. The housing 510 is made of high strength material, such as steel, which can support the weight of the sample and can stand the pressure transmitted from the rigid confining case 520 when the pressure jacket 530 is pressurized.

An ultrasonic signal generation and recording system 60 is included with the system 5 and has four major components: a computer 560 with an application program 561 installed on it, a pulser/receiver 565 that sends and receives signals as directed by the computer 560, a switch 566 that connects an electric conduction path between the pulser/receiver and one or more transducers 544, and a Data Acquisition unit (DAQ) 568 that is configured to receive signals from the transducers 544. The DAQ 568 can include a digitizer, oscilloscope, or both. The computer 560 is connected to the pulser/receiver 565, the switch 566, and the DAQ 568. The pulser/receiver 565 is connected to the computer 560, the switch 566, and the DAQ 568. The switch 566 is connected to the pulser/receiver 565, the computer 560, and the ultrasonic transmitters 541 and 551 through the bundles of transmitting cables 543 and the transmitting cables 552. The DAQ 568 is connected to the pulser/receiver 565, the computer 560, and the ultrasonic receivers 545 and 555 through the bundles of receiving cables 547 and 557.

A fluid pressure supply and control system 70 is also included with the system 5 has a source of pressurized fluid 570, pressure gauges 571 and 575 that monitor the pressure in the system 70, a flexible, high strength tube 572 that directs fluid to a desired location along three branches 577, 578, and 579, a pressure regulator 573 that controls the pressure to be at a desired threshold, a valve 574, and a bleeding valve 576 that are used to control the system 70. The fluid pressure supply and control system 70 supplies and maintains a required pressure to the pressure jacket during testing operations. The pressurized fluid is in connection with the center jacket member 531, right jacket member 537, and left jacket member 538 of the pressure jacket 530 through the tube 572 and the branches 577, 578, and 579. The pressure regulator 573, the valve 574, the pressure gauge 575, and the bleeding valve 576 are fitted on the tube 572. The pressure of the supplied pressurized fluid is monitored by a pressure gauge 571. The pressurized fluid is supplied to the pressure jacket 530 through the tube 572 and the branches 577, 578 and 579. The applied pressure to the pressure jacket 530 is adjusted by the pressure regulator 573 and monitored with the pressure gauge 575.

Figure 15:
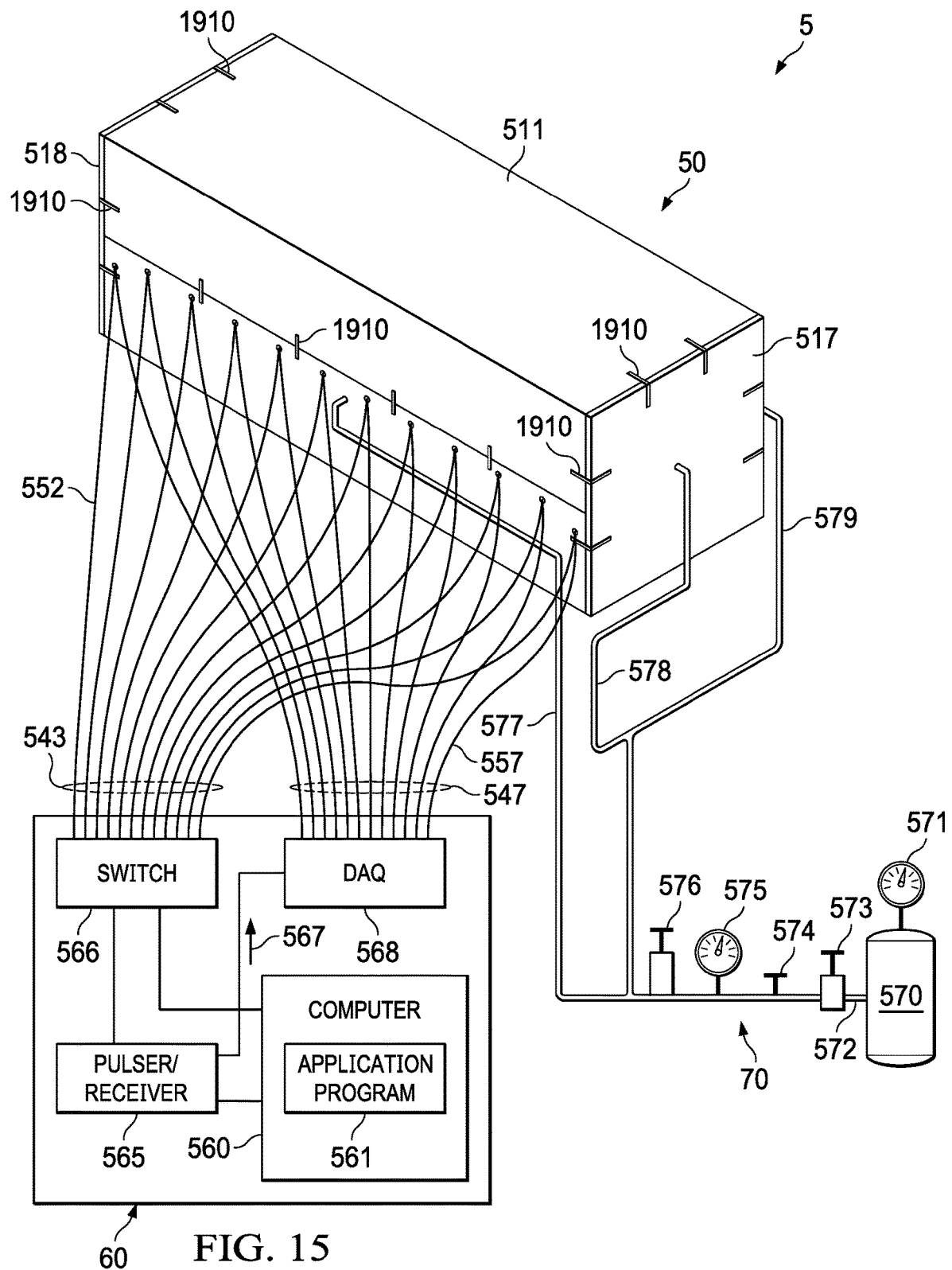
FIG. 15 is a schematic diagram of an example core testing system.

As previously mentioned, FIG. 2 is a longitudinal cross-sectional view of a sample chamber 50 when the sample chamber 50 is closed. The rigid confining case 520 has a center casing member 521, a right casing member 527, and a left casing member 528. The center casing member 521 has a shape of a circular tube when it is closed. In the illustrated example, the right casing member 527 and the left casing member 528 are identical and have a shape of a circular tube with the same cross section and wall thickness as the center casing member 521, but different cross-sections can be used based on the sample cross-section shape without departing from the scope of the disclosure. The right casing member 527 and the left casing member 528 are dimensionally configured to accommodate the right jacket member 537 and the left jacket member 538. That is, the right casing member 527 and the left casing member 528 have a height just enough to accommodate the right jacket member 537 and the left jacket member 538 respectively. The right casing member 527 is fixed to the right housing member 517 and the left casing member 528 is fixed to left housing member 518. This arrangement makes the members of the rigid confining case 520 move together with the members of the housing 510. The rigid confining case 520 is made of stiff and high strength material, such as a steel with high strength and Young's modulus, such that it can stand the pressure transmit from the pressure jacket with no or negligible deformation. When the sample chamber 50 is closed for a measurement, it is securely locked by lock mechanisms 1910 (FIG. 15). In some implementations, the lock mechanism 1910 can be a latch or clasp.

The pressure jacket 530 has a center jacket member 531, a right jacket member 537 configured to be positioned on a first side of the center jacket member 531, and a left jacket member 538 configured to be positioned on a second side of the center jacket member 531. The first side of the center jacket member 531 and the second side of the center jacket member 531 are opposite of one another. Each member of the pressure jacket 530 is a hollow air tight bag, made of strong, flexible, elastic material, such as reinforced rubber, that can stand the pressure when a required pressure is applied. The pressure jacket 530 is pressurized during testing operations and unpressurized otherwise. The center jacket member 531 of the pressure jacket 530 is attached to the inner side of the center casing member 521 of the rigid confining case 520, for example, with press studs. The center jacket member 531 is at most the same length as the center casing member 521 of the rigid confining case 520. If it is detached from the center casing member 521 and fully opened, the center jacket member 531 has a flat, rectangular shape. When the sample chamber 50 is closed and the center jacket member 531 is pressurized, the center jacket member 531 takes the shape of the center casing member 521, and has a shape of a circular tube.

Figure 3:
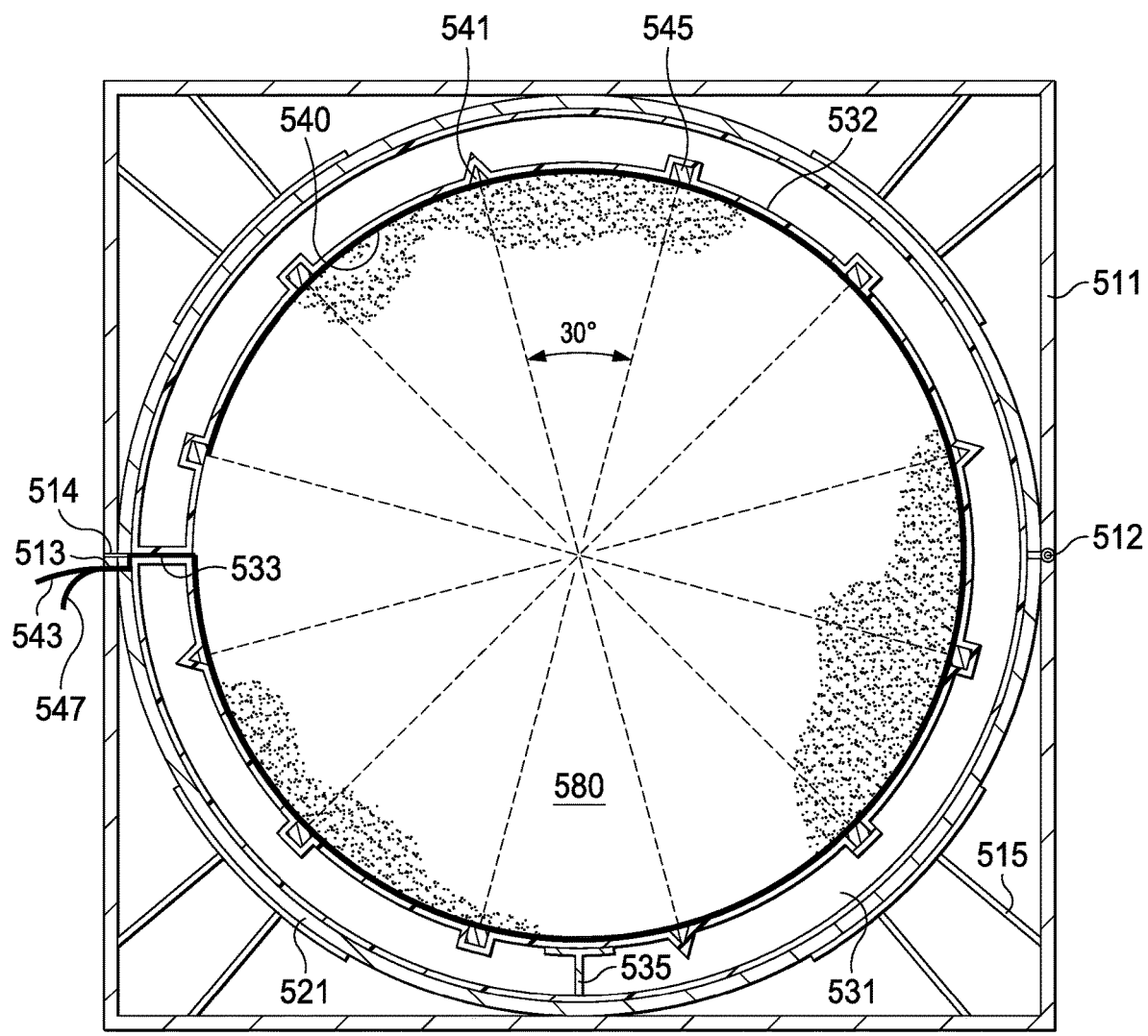
FIG. 3 is a schematic diagram showing a cross-sectional view transverse to an example sample within an example sample chamber.

FIG. 3 is a half cross-sectional view of the sample chamber 50 when the sample chamber 50 is closed. In the example, the center casing member 521 has an upper part and lower part of same dimensions. The upper part of the center casing member 521 is fixed to the upper part of the center housing member 511 at contact locations and by four supporting frames 515. The lower part of the center casing member is fixed to the lower part of the housing 510 at the contact locations and by four supporting frames 515. Inside the center jacket member 531, a girder 535 is fixed to the bottom middle, along the longitudinal direction, to support the weight of the sample 580. On top of the girder 535, some lateral beams can hold the sample. The beams may not be on the same circumferences with the transducer rings 540. Small holes along the girder can, in some implementations, homogenize the pressure within the pressure jacket.

The right jacket member 537 is fixed within the right casing member 527 and left jacket member 538 is fixed within the left casing member 528 of the rigid confining case 520, for example, by using press studs. In the illustrated example, when the pressure jacket members are pressurized, the right jacket member 537 and the left jacket member 538 have the same height as the right casing member 527 and the left casing member 528. If the jacket 530 is unpressurized, due to its flexibility, the upper half of the center jacket member 531 of the pressure jacket 530 can move together with the upper part of the center casing member 521. The right jacket member 537 also moves with the right casing member 527, and the left jacket member 538 of the pressure jacket 530 moves together with the left casing member 528.

Ultrasonic transducers 544 and electronic cables connecting the transducers 544 are embedded, overlaid, or otherwise run across an inner skin of the three members of the pressure jacket 530 with the surfaces of the transducers 544 exposed such that when a sample is loaded, the sample chamber 50 is closed and the pressure jacket is pressurized, the surfaces of the transducers 544 are in direct contact with the sample 580. A same pressure is applied to the three members of the pressure jacket 530 during the setup and the run of a test. All the transducers 544 are pressed against the sample by the same applied pressure resulting in a consistent and stable contact of the transducers 544 to the sample. Transducers 544 are not arranged on the top the lateral beams of the girder 535 to avoid bearing any weight of the sample. Such an arrangement results in the same pressing pressure on all the transducers 544.

Figure 4:
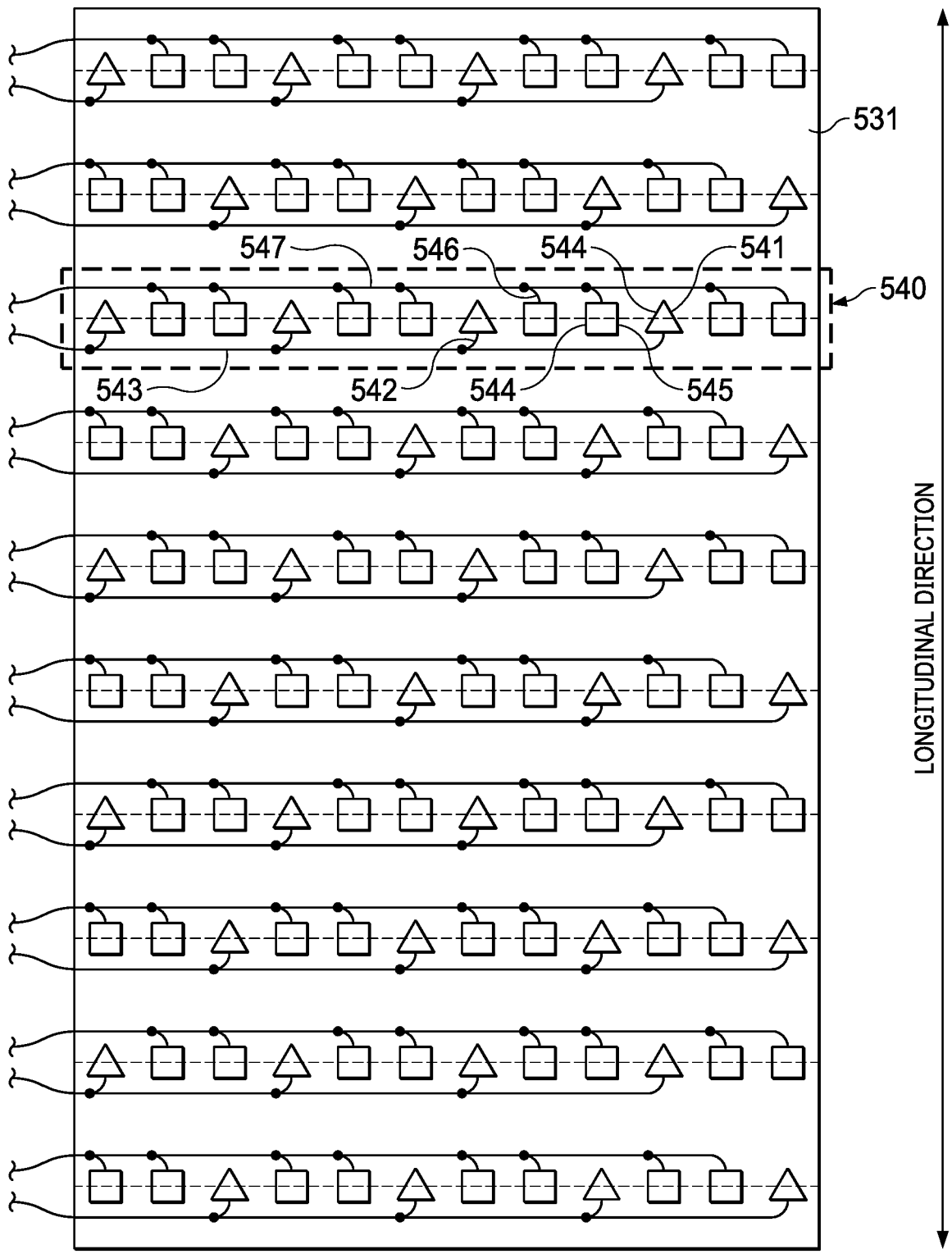
FIG. 4 is a schematic diagram of a center jacket member with an arrangement of transmitters and receivers.

FIG. 4 shows the top plane view of an example arrangement of ultrasonic transducers 544 on the inner skin of the center jacket member 531 when the center jacket member 531 is unfolded. On the center jacket member 531, transducers 544 are arranged into rings 540. For the illustrated arrangement, there are ten transducer rings 540. Each of the transducers 544 can be a transmitter 541, a receiver 545, or both. On one of the rings 540, there are four ultrasonic transmitters 541 and eight ultrasonic receivers 545 arranged in a pattern of one transmitter 541 separated by two receivers 545. The transducers 544 are separated by equal distance, thus forming a ring with a center angle of 30° between any two neighboring transducers 544. Each of the ultrasonic transmitters 541 are connected to an electronic cable 542. These electronic cables 542 are bundled together to form a bundle of cables 543. For convenience, these bundles 543 are termed bundles of transmitting cables. Each of the ultrasonic receivers 545 are connected to an electronic cable 546. These electronic cables 546 are bundled together to form a bundle of cables 547. For convenience, these bundles 547 are termed bundles of receiving cables. The transducers 544 and associated cables are embedded on the inner skin 532 of the center jacket member 531 (FIG. 3). For the illustrated transducer 544 arrangement, a first transducer ring 540 starts with a transmitter 541 and then the next ring with two receivers 545 alternating thereafter.

Figure 5A:
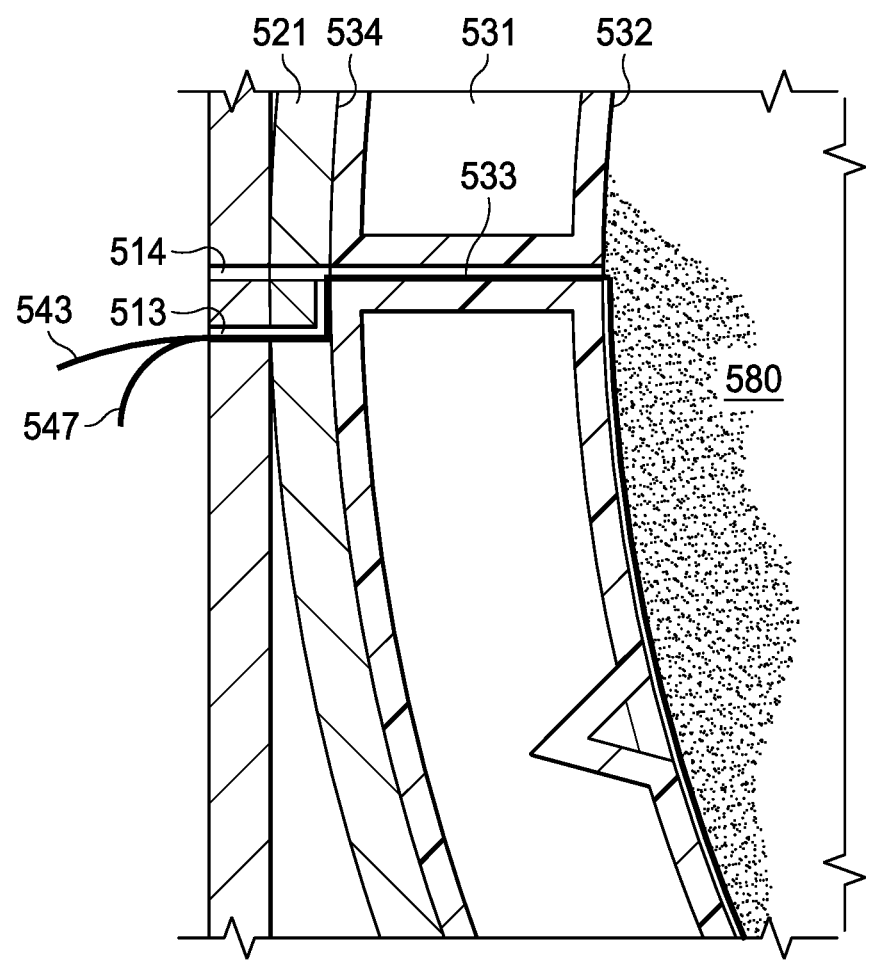
FIGS. 5A-5B are detailed cross-sectional views of parts around a cable hole according to an example implementation.

FIG. 5A is a detailed cross-sectional view of parts around a cable hole 513, which is for routing the cables out of the sample chamber 50, according to the example implementation. At the end of a transducer ring 540, both the bundle of transmitting cables 543 and the bundle of receiving cables 547 are embedded on the end surface 533 of the center jacket member 531 of the pressure jacket. They are then fixed downwards between the outer skin 534 of the pressure jacket and the center casing member 521 of the rigid case and go through a hole 513 to come out of the sample chamber 50. The holes 513 go through the rigid case and the housing and are located just below the joint 514.

Figure 5B:
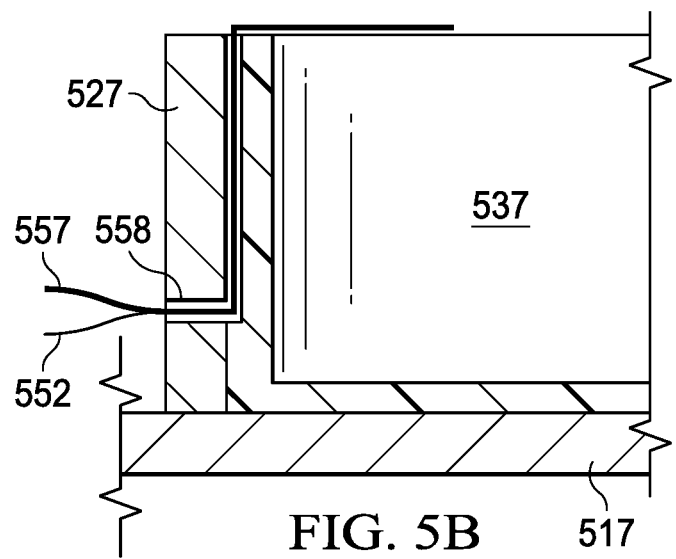

FIG. 5B is a detailed sectional view of parts around a cable hole 558. A set of transducers 544 and electronic cables are embedded on the top skin of the right jacket member 537 and the left jacket member 538 of the pressure jacket 530. The transducers 544 can be arranged in different ways. For example, for the implementation shown in FIG. 1, one ultrasonic transmitter 551 and four ultrasonic receivers 555 are embedded on the top skin of the right jacket member 537 of the pressure jacket 530. The four receivers 555 are arranged in a circle with the transmitter 551 in the center. The receiver's circle is not too big, such that when the sample chamber 50 is closed, the receivers are within the contact area of the sample 580. An electronic cable is connected with each of the transducers 544. The electronic cables 556 connecting to the receivers 555 are bundled together. The cable 552 connecting the transmitter 551 is termed a transmitting cable. The transmitting cable 552 and the bundle 557 of receiving cables are embedded in the top skin of the right member of the pressure jacket. The transmitting cable 552 and the bundle 557 are routed out of the sample chamber 50 by the following sequential arrangement: being fixed downwards between the skin of the pressure jacket and the right casing member 527 of the rigid case, going through a hole 558, passing beneath the center casing member 521 of the rigid case 520 and then a hole 559 on the center housing member 511 of the housing 510. While the illustrated example shows one example of appropriate cable routing for the described application, other routes can be used. The hole 558 is just beneath the top edge of the right casing member 527 of the rigid case 520. There is also one transmitter and same or different number of receivers embedded on the left jacket member 538 of the pressure jacket 530.

According to the implementation illustrated in FIGS. 1-2, the center chamber member 51 of the sample chamber 50 includes the center housing member 511 of the housing 510, the center casing member 521 of the rigid case 520, the center jacket member 531 of the pressure jacket 530, and the embedded transducers 544 and electronic cables. The right chamber member 57 of the sample chamber 50 includes the right housing member 517 of the housing 510, the right casing member 527 of the rigid case 520, the right jacket member 537 of the pressure jacket 530, and the embedded transducers 544. The left chamber member 58 of the sample chamber 50 has similar components to the right chamber member 57. When the sample chamber 50 is closed for a measurement, it is securely locked by lock mechanisms 1910 (FIG. 15), such as a latch or clasp.

Several different arrangements of transmitters and receivers can be used on the left and right member of the pressure jacket. The arrangement of the transducers 544 on the center jacket member 531 of the pressure jacket can have various arrangements as well. Such implementations are described later within this disclosure.

Figure 6A:
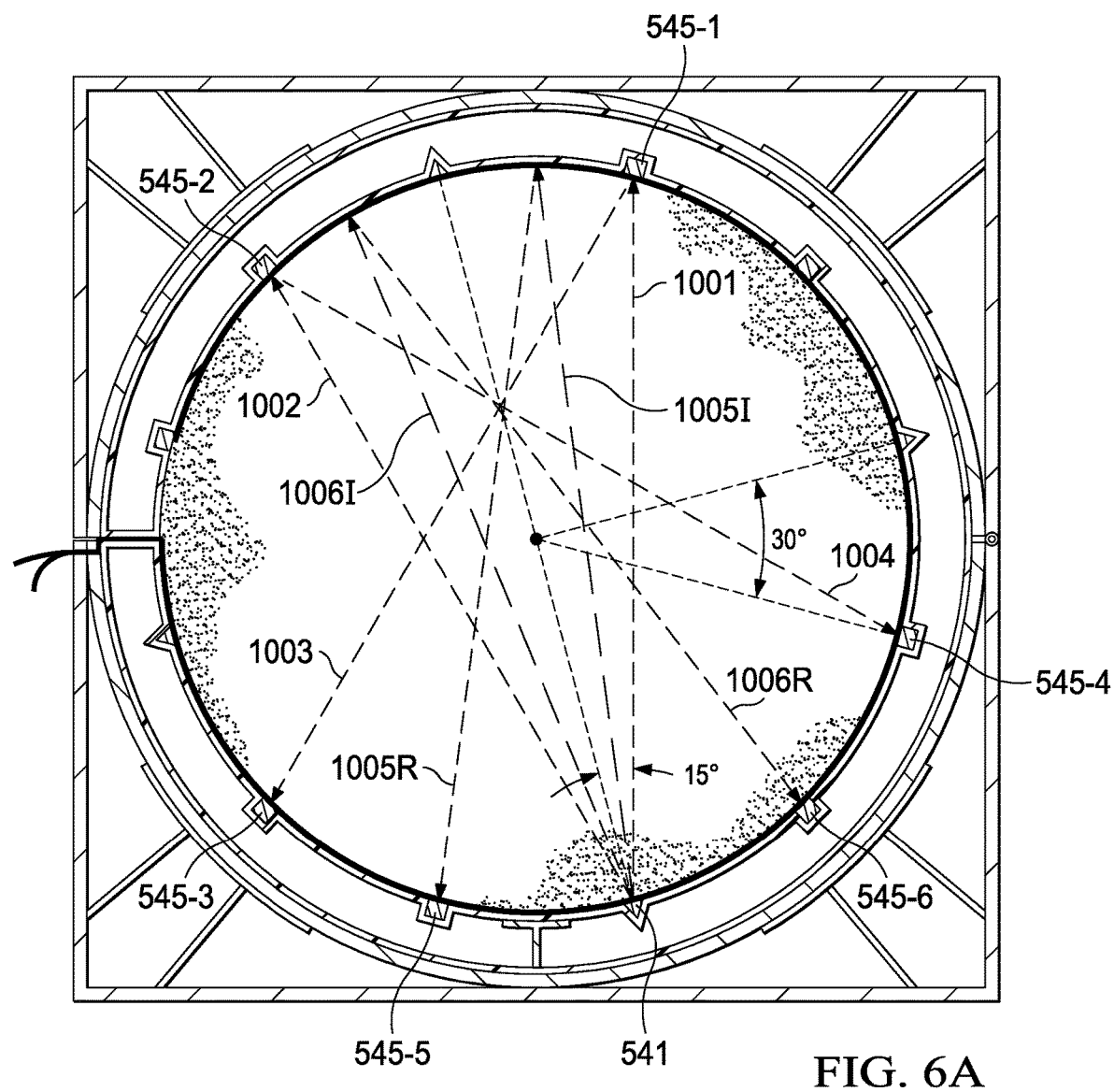
FIGS. 6A-6B illustrate example signal paths through a sample.
Figure 6B:
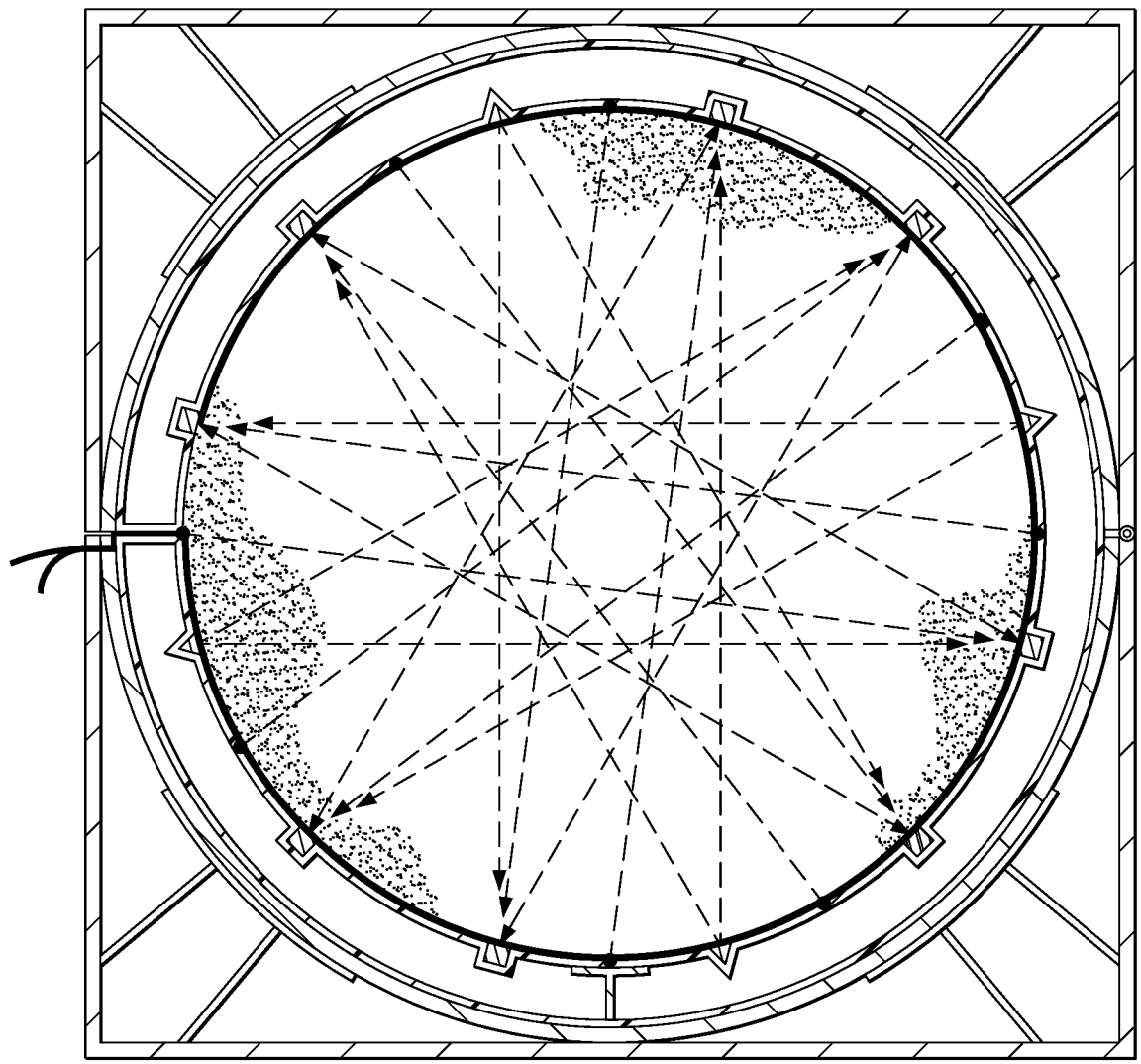

The example transducer arrangement shown in FIG. 4 shows a transducer ring 540 with four ultrasonic transmitters and eight ultrasonic receivers arranged in a pattern of one transmitter 541 separated by two receivers 545. The transducers 544 are separated by equal distance, thus forming the ring with a center angle of 30° between any two neighboring transducers 544. FIG. 6A shows a set of ray-paths of ultrasonic waves originated from a transmitter and picked up by receivers on a transducer ring 540. In the illustrated example, an angle of beam spread of the transmitters 541 is greater than 15°. The beam spread of the transmitters is configured prior to installation. With this angle of beam spread, on a ring 540, when an ultrasonic transmitter 541 transmits a pulse of ultrasonic waves, the ultrasonic wave signals will reach two receivers 545-1 and 545-2 along ray-paths 1001 and 1002, and are picked up by the receivers, respectively. The ultrasonic waves are reflected at the boundary of the sample 580. The reflected ultrasonic waves reflected at the receivers 545-1 and 545-2 locations will travel along ray-paths 1003 and 1004 and are picked up by the receivers 545-3 and 545-4, respectively. Receiver 545-5 also receives a reflected ultrasonic wave signal traveling along the ray-path 10051-1005R, so does the receiver 545-6 along the ray-path 10061-1006R. In total, when a transmitter 541 is fired, two receivers will receive incident ultrasonic wave signals and four receivers will receive reflected ultrasonic wave signals. When all the transmitters 541 are fired one by one at a short time interval, each of the receivers 545 will receive an incident ultrasonic wave signal and two reflected ultrasonic wave signals, as shown in FIG. 6B. The acoustic properties along different directions, such as acoustic velocities, can be calculated from the received signals. In the transducer arrangement illustrated in FIGS. 6A-6B, each of the receivers receives both an incident and two reflected signals.

Figure 7:
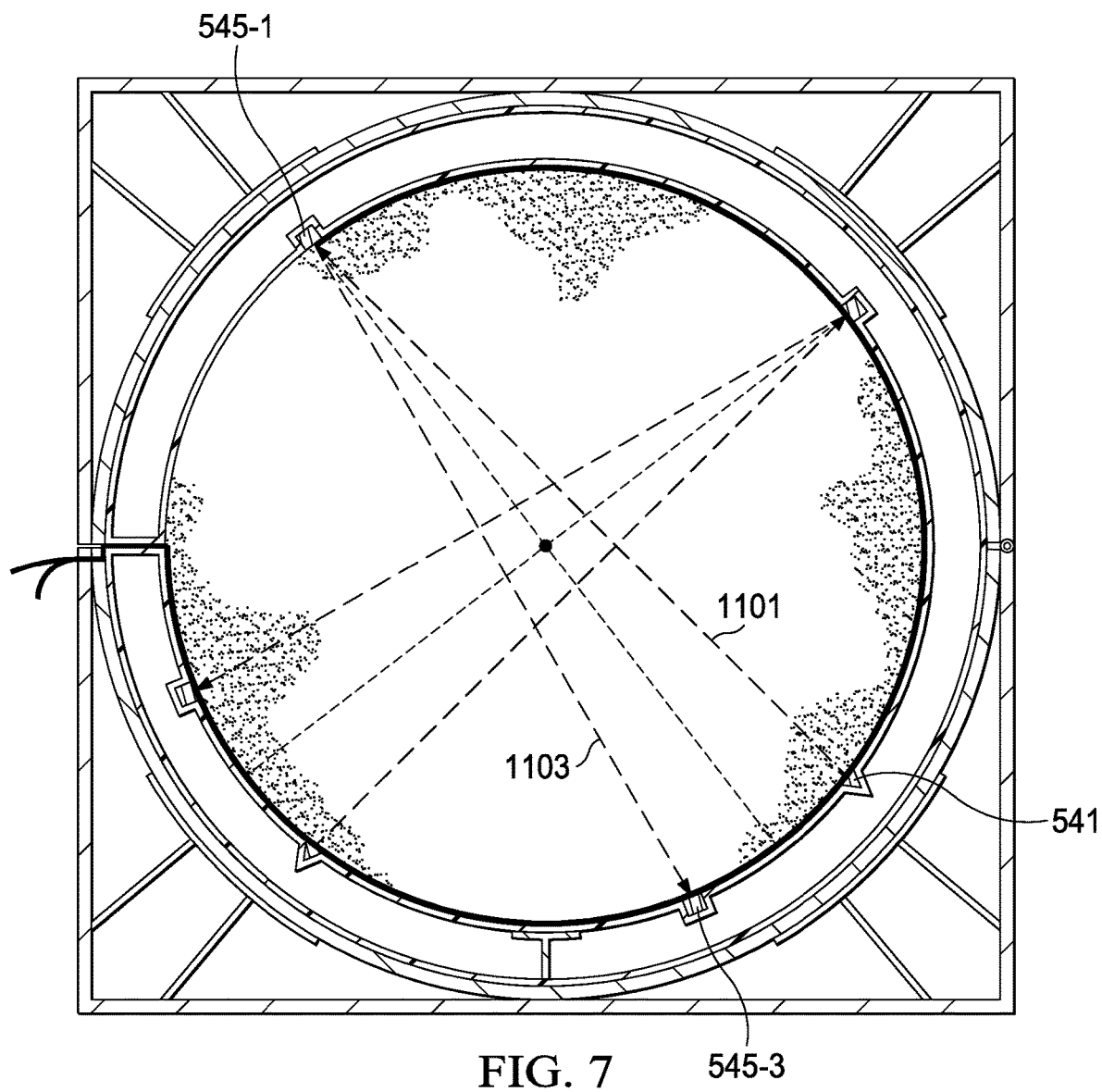
FIG. 7 example signal paths utilizing a transducer arrangement with two transmitters and four receivers on a transducers ring.

FIG. 7 shows an example transducer arrangement with two transmitters and four receivers on a transducer ring 540. On a ring, each of the two ultrasonic transmitters 541 is coupled with two ultrasonic receivers 545-1 and 545-3. They form an isosceles triangle, such that when an ultrasonic signal originated from the transmitter 541 is reflected at the receiver 545-1 location, the reflected ultrasonic signal reaches to the receiver 545-3. When the ultrasonic transmitter 541 transmits a pulse of ultrasonic waves, the ultrasonic wave signal will reach the receiver 545-1 along a ray-path 1101, and is picked up by the receiver 545-1. The ultrasonic waves are reflected at the boundary of the sample 580. The reflected ultrasonic wave signal reflected at the receiver 545-1 location will travel along a ray-path 1103 and is picked up by the receiver 545-3. When the two transmitters 541 are fired one by one at a short time interval, each of the receivers 545 will receive either an incident ultrasonic wave signal or a reflected ultrasonic wave signal. The acoustic properties along different directions, such as acoustic velocity, can be calculated from the received signals. In the transducer arrangement illustrated in FIG. 7, each of the receivers only receives one (either the incident or reflected) signal. Compared with the transducer arrangement shown in FIG. 3 and FIGS. 6A-6B, this arrangement has half the number of transmitters and receivers, but only a quarter of measurements.

Figure 8:
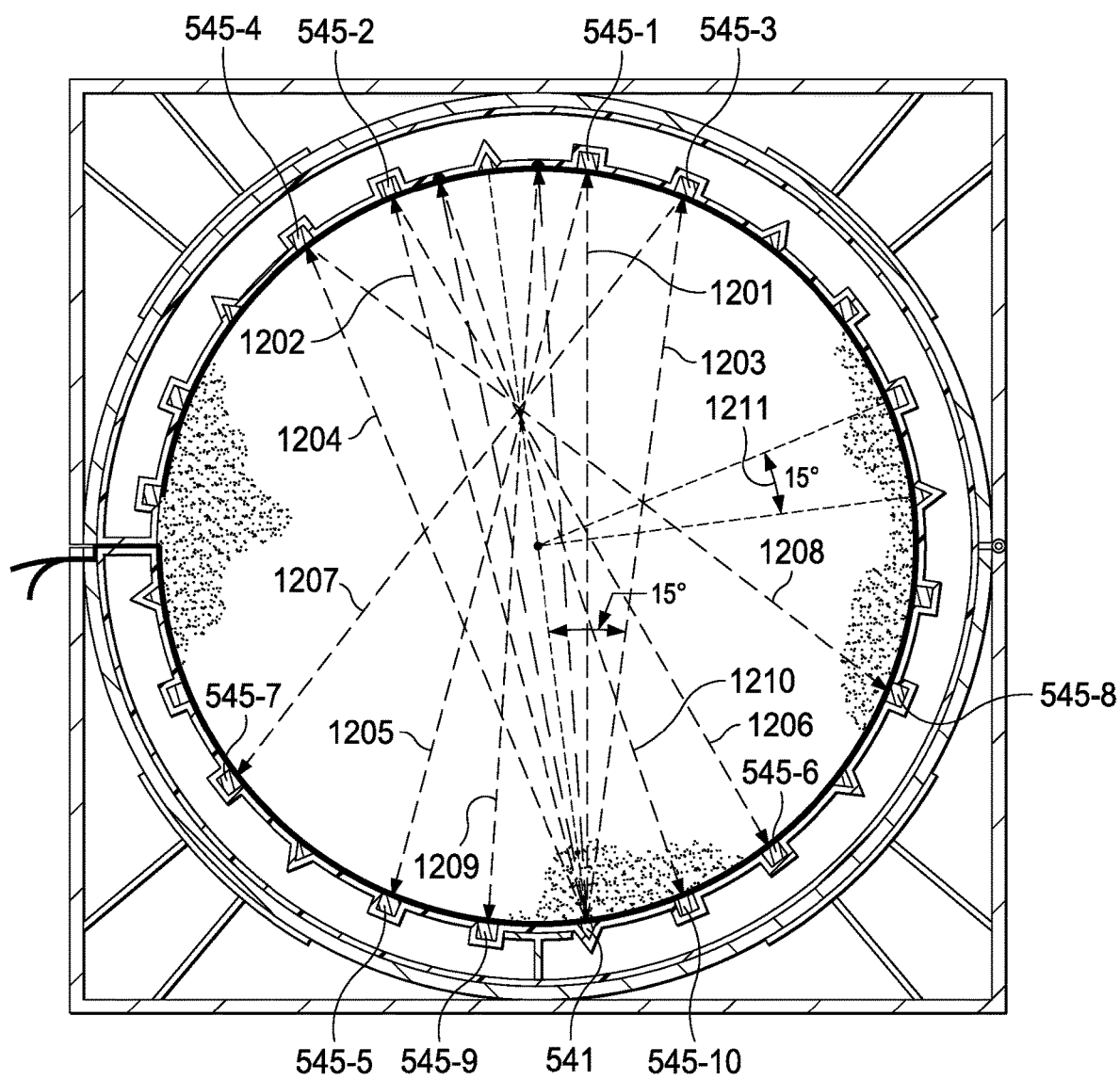
FIG. 8 illustrates example signal paths through a sample.

FIG. 8 shows an example transducer arrangement on a transducer ring 540 with eight ultrasonic transmitters 541 and sixteen ultrasonic receivers 545 arranged in a pattern of one transmitter 541 separated by two receivers 545. The transducers 544 are placed in equal distance, thus forming the ring with a center angle 1211 of 15° between any two neighboring transducers 544. The angle of beam spread of the transmitters 541 is greater than 15°. With this angle of beam spread, on a ring, when an ultrasonic transmitter 541 transmits a pulse of ultrasonic waves, the ultrasonic wave signals will reach four receivers 545-1, 545-2, 545-3, and 545-4 along ray-paths 1201, 1202, 1203, and 1204. The ultrasonic waves are reflected at the boundary of the sample 580. The reflected ultrasonic waves reflected at the receivers 545-1, 545-2, 545-3, and 545-4 locations will travel along ray-paths 1205, 1206, 1207, and 1208 and are picked up by the receivers 545-5, 545-6, 545-7, and 545-8, respectively. Receivers 545-9 and 545-10 also receive a reflected ultrasonic wave signal traveling along the ray-path 1209 and 1210, respectively. In total, when a transmitter 541 is fired, the ultrasonic signals are received by ten receivers on the ring. When all the transmitters 541 are fired one by one at a short time interval, each of the receivers 545 will receive two incident ultrasonic wave signals and three reflected ultrasonic wave signals. The acoustic properties along different directions, such as acoustic velocity, can be calculated from the received signals.

In some implementations, a 3D measurement can be recorded. In order to make a 3D measurement, signals transmitted by a transmitter 541 should be received by receivers 545 attached to a different transducer ring 540. To do so, transducer rings 540 are placed with a small interval space between two neighboring rings, such that the power of ultrasonic wave transmitted from a transmitter 541 can sufficiently reach some receivers 545 on the neighboring transducer rings 540.

Figure 9:
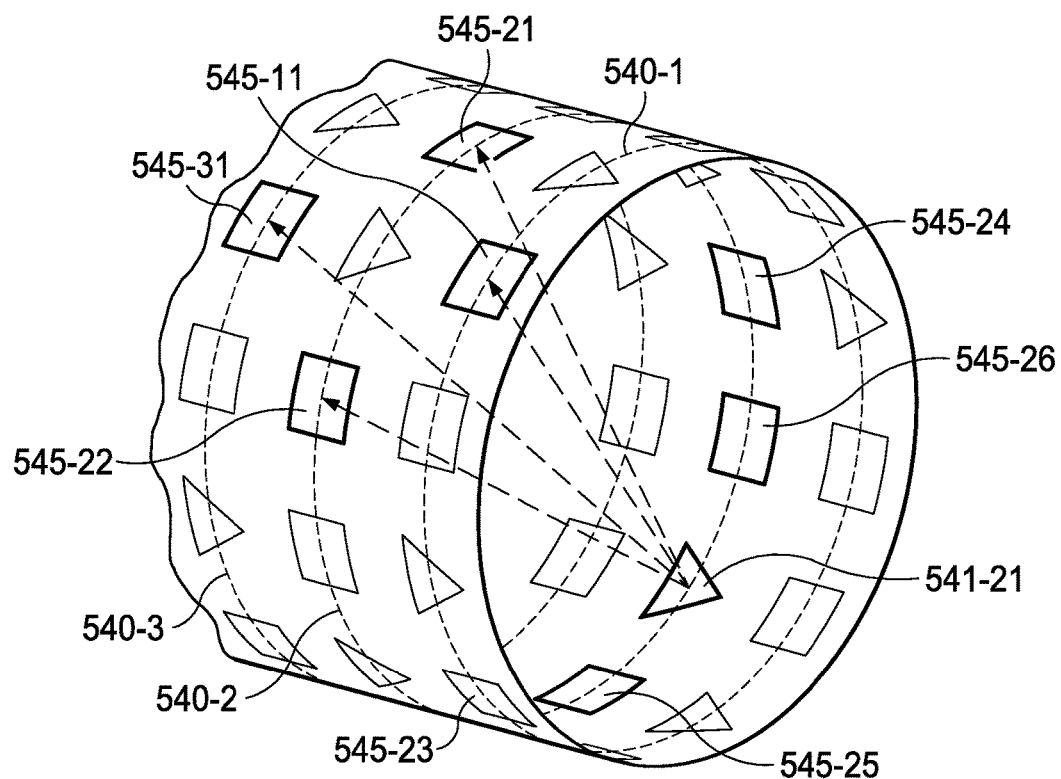
FIG. 9 is a schematic diagram illustrating an example arrangement of transmitters and receivers positioned around a sample.

FIG. 9 is a perspective view of an example arrangement of transducers suitable for 3D measurement. In the illustrated implementation, the first three transducer rings 540 are shown. The transducer arrangement on a ring is similar to the arrangement shown in FIG. 4. On each transducer rings 540, there are four ultrasonic transmitters 541 and eight ultrasonic receivers 545 arranged in a pattern of one transmitter 541 separated by two receivers 545. The transducers 544 are separated by equal distance, thus forming the ring with a center angle of 30° between any two neighboring transducers 544. A transducer ring 540 starts with a transmitter 541 and then the next ring with two receivers 545 to ensure the ultrasonic waves transmitted from a transmitter to reach receivers on the neighboring transducer rings 540.

Figure 10:
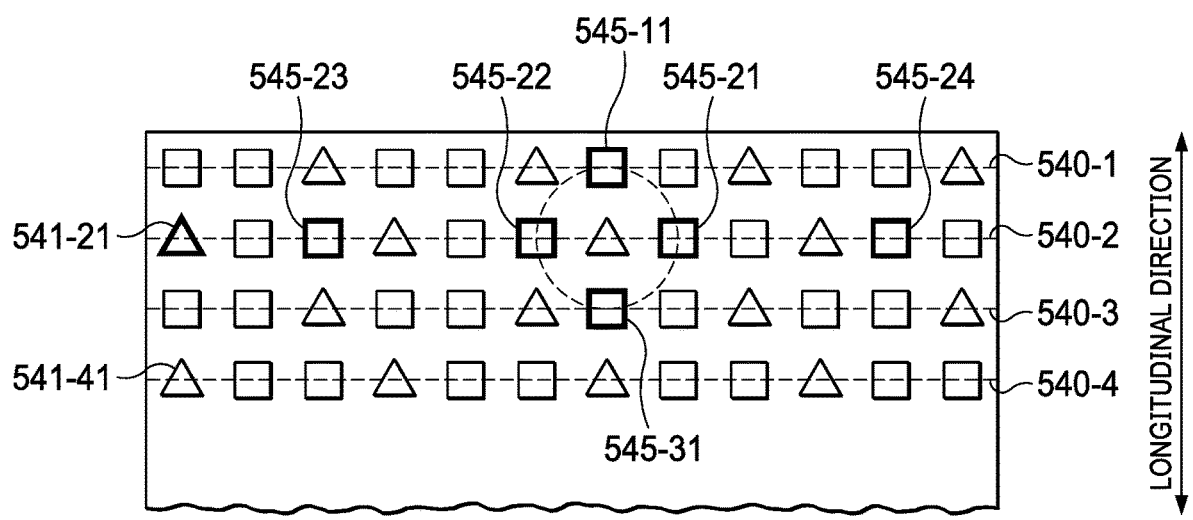
FIG. 10 is a schematic diagram of a center jacket member with an arrangement of transmitters and receivers.

FIG. 10 is the top plane view of the transducer arrangement in FIG. 9, showing the transducer arrangement on the inner skin of the center jacket member 531 when the pressure jacket 530 is unfolded. The angle of beam spread of the transmitters 541 is greater than 15°. For this particular transducer 544 arrangement, the distance between two neighboring transducer rings 540 is the same as between two transducers 544 of a ring. Therefore, when a transmitter 541-21 on a ring 540-2 transmits a pulse of ultrasonic waves, the ultrasonic waves reach two receivers 545-21 and 545-22 on the same ring 540-2, as well as two receivers 545-11 and 545-31 on the neighboring rings 540-1 and 540-3, respectively. The receivers 545-23, 545-24, 545-25, and 545-26 on the ring 540-2 also receive reflected ultrasonic waves reflected at the boundary of the sample.

To construct ultrasonic computer tomography imaging, the ray-paths of the ultrasonic waves are picked up by the receivers 545, intersect one another. Richness of the information of the image depends on the number of ultrasonic wave rays intersecting at one point. Resolution of the image depends on the number of the intersection points and evenness of the distribution of the intersection points within the volume of the sample. For a transducer arrangement shown on FIG. 6B, the number of the intersection points is not large enough for ultrasound computer tomography imaging. Also, the intersection points distribute around the center of the sample. That is, they do not spread evenly. The number of ultrasonic wave rays intersecting at one point, the number of the intersection points, and distribution evenness of the intersection points can be enhanced by increasing the number of transducers 544 on a ring, using transmitters with a wide angle of beam spread, attaching transmitters with a tilting angle, arranging transmitters and receivers on different rings, or any combination of the aforementioned methods.

Figure 11:
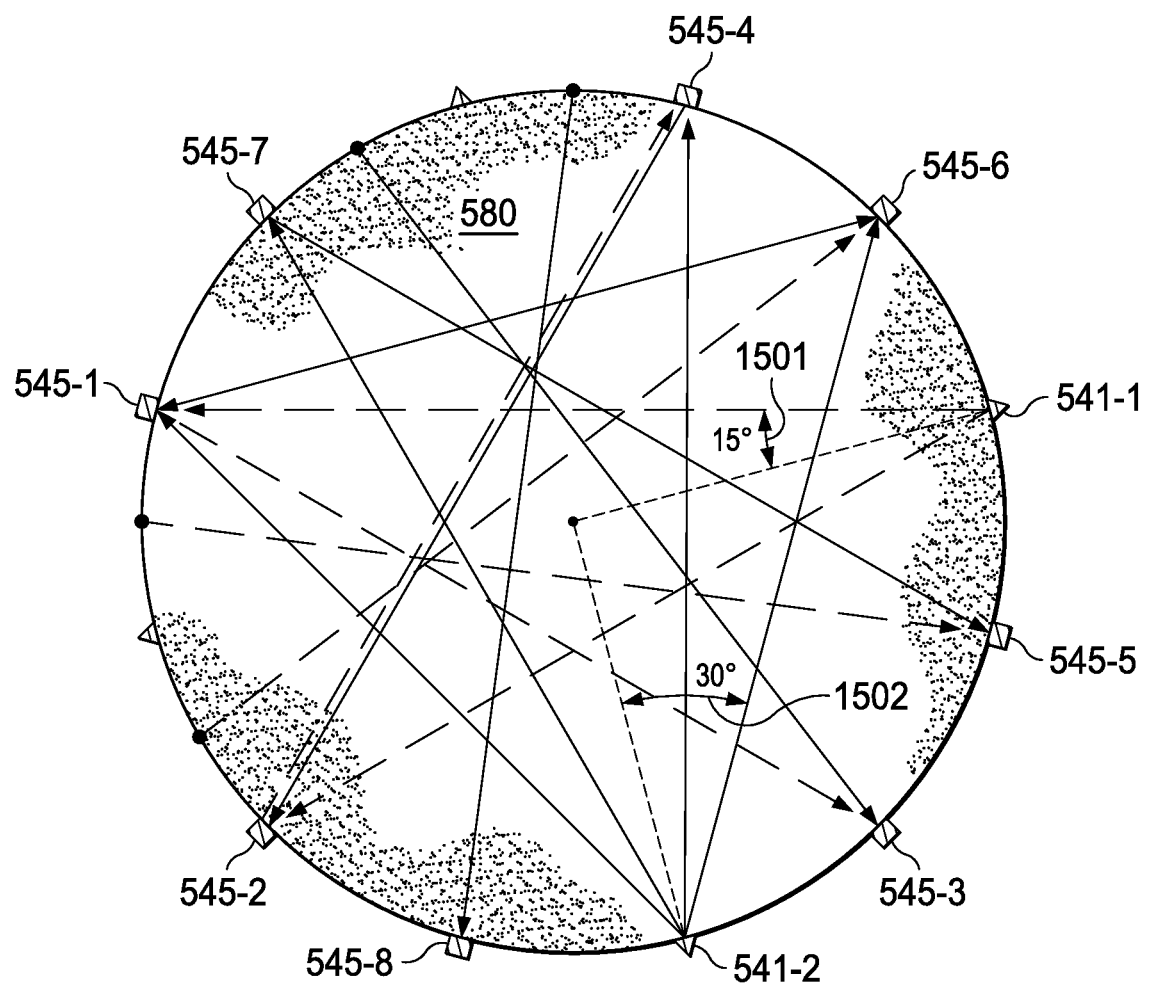
FIG. 11 illustrates example signal paths through a sample.

FIG. 11 shows ray-paths of received ultrasonic waves originated from a transmitter with a 15° angle of beam spread 1501, represented by dashed lines, and those from a transmitter with a 30° angle of beam spread 1502, represented by solid lines. For the transmitter 541-1 with a 15° angle of beam spread, there are six signals picked up by receivers, two incident ones picked up by receivers 545-1 and 545-2 and four reflected ones by receivers 545-3, 545-4, 545-5, and 545-6. For the transmitter 541-2 with a 30° angle of beam spread, ten signals are picked up, with four incident ones picked up by receivers 545-1, 545-7, 545-4, and 545-6; six reflected signals picked up by receivers 545-1, 545-2, 545-8, 545-3, 545-5, and 545-6. The larger number of ray-paths results in more intersection points. The intersection points spread more towards the edge of the sample 580. That is, the intersection points distribute more evenly.

In the previously discussed situations, transducers 544 (transmitters and receivers) are normally attached directly to the sample. That is, a transducer 544 is embedded on the center member 531 of the pressure jacket 530 in such way that the transducer's face is normal to the axis of sample, that is, parallel to the surface of the sample.

Figure 12:
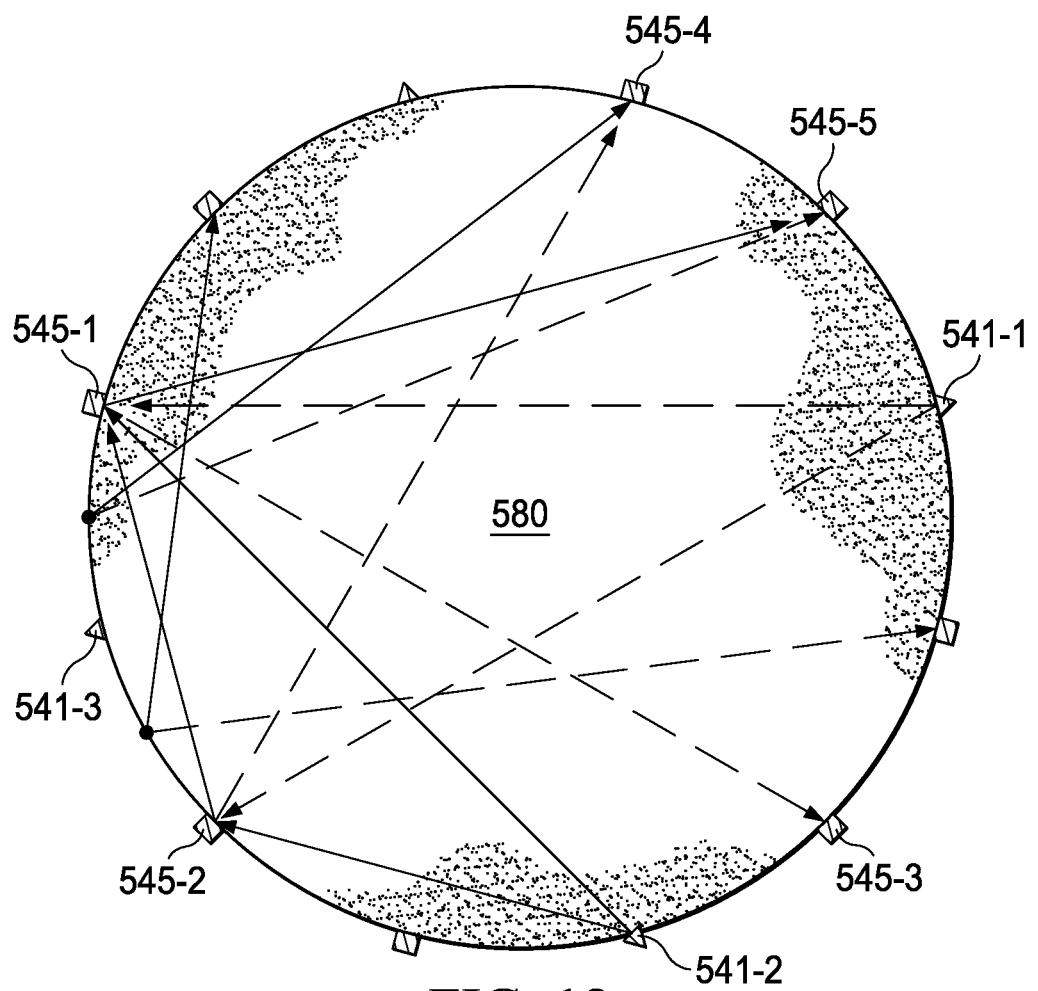
FIG. 12 illustrates example signal paths through a sample.

FIG. 12 shows the ray-paths of ultrasonic waves originated from a normally attached transmitter 541-1, represented by dashed lines, and those from a tilted transmitter 541-2, represented by solid lines. The face of the tilted transmitter is not parallel to the surface of the sample 580. There are six ray-paths of the received ultrasonic signals for the ultrasonic waves generated from both transmitter 541-1 and 541-2. Compared with the ray-paths of the ultrasonic waves originated from the normally attached transmitter 541-1, the ray-paths of the ultrasonic waves originated from the tilted transmitter 541-2 travel away from the center of the sample, thus resulting in more evenly distributed intersection points. Therefore, tilted attachment of some transmitters enhances the distribution evenness of the intersection points.

Figure 13:
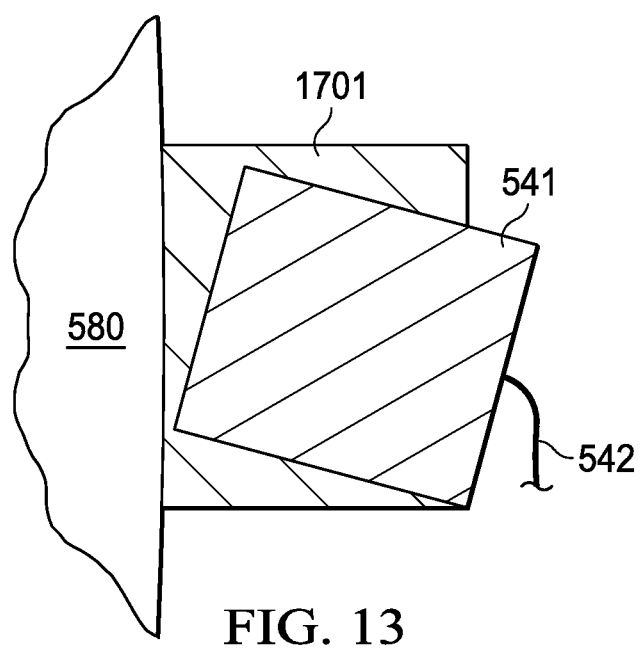
FIG. 13 is a schematic diagram of a transmitter or receiver positioned at an angle relative to a surface of a sample.

A tilted transmitter can be fitted by using an adaptor. FIG. 13 schematically shows an example mounting mechanism for such an application. An adaptor 1701 is obliquely mounted on a transmitter 541 in such a way that the surface of the adaptor 1701 is in parallel contact with the sample 580, while the face of the transmitter 541 is in an angle to the surface of the sample 580. The transmitter 541 with the mounted adaptor 1701, together with the electronic cable 542, are embedded on the inner skin of the center jacket member 531 of the pressure jacket.

There is a limitation by arranging both transmitters 541 and receivers 545 on a same ring for 3D ultrasound computer tomography imaging. Referring back to FIG. 12, when ultrasonic waves emitted from a transmitter 541-1 arrives to the opposite side of the sample 580, they cannot be received at the transmitter 541-3 location, simply because 541-3 is a transmitter, not a receiver. If a receiver is located at the location 541-3, a ray-path can be established between the transmitter 541-1 and the receiver, which will result in more intersection points. As a reminder, FIG. 9 illustrates an example of ultrasonic wave transmission between rings. When the ultrasonic waves originated from the transmitter 541-21 are reflected at the receiver 545-31 location, they travel to the fourth ring and reach to the location where a transmitter 541-41 is located (FIG. 10). These signals cannot be used since they are not picked up by a receiver.

Figure 14:
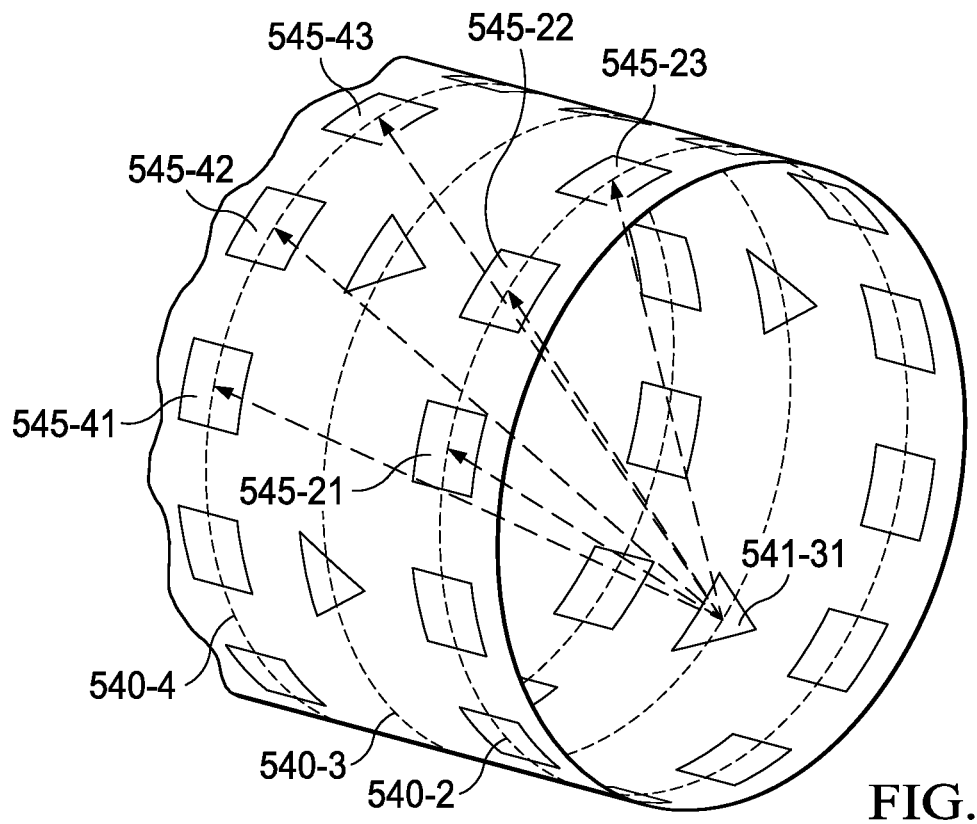
FIG. 14 is a schematic diagram of a center jacket member with an arrangement of transmitters and receivers.

FIG. 14 is a perspective view of an arrangement of transducers 544 for 3D computer tomography imaging. For the illustrated transducer arrangement, transmitters and receivers are arranged on different rings. That is, there are two types of transducer rings 540: transmitter rings, which only contain transmitters 541, and receiver rings, which only contain receivers 545. Transmitter rings and receiver rings are arranged in an alternate way, that is, one transmitter ring is adjacent a receiver ring. A first ring is a transmitter ring, which is not shown, the second 540-2 a receiver ring, third 540-3 a transmitter ring, and fourth 540-4 a receiver ring, so on so forth. As illustrated, transducer rings 540 are equally spaced. In some implementations, spacing between transducer rings 540 can vary. The space between neighboring rings is small enough that the ultrasonic waves transmitted from a transmitter 541 can reach some receivers 545 on the neighboring receiver rings. For example, the ultrasonic waves transmitted from a transmitter 541-31 on the ring 540-3 reach receivers 545-21, 545-22 and 545-23 on the ring 540-2, and receivers 545-41, 545-42 and 545-43 on the ring 540-4. Some receivers 545 on the next receiver ring will also receive reflected ultrasonic wave signals.

The transducers 544 embedded on the center member 531 of the pressure jacket 530 can have different arrangements according to the requirements of actual applications. The functions of the ultrasonic signal generation and recording system 60 of the system 5 are to generate high frequency electric pulses, to receive the transmitted incident and reflected ultrasonic signals, and to record and process the received ultrasonic signals to derive required information.

FIG. 15 is a schematic diagram of the system 5 after a sample has been installed, securely locked, and is ready for a measurement. During operations, an application program 561 sends a command to the switch 566 to instruct the switch 566 to make a connection between the pulser/receiver 565 and one of the transmitters 541 or 551. The application program 561 sends a command to the pulser/receiver 565 to generate a high-voltage pulse. The electric pulse is relayed to the transmitter by the switch 566 through one of the transmitting cables 543. When the transmitter 541 or 551 is pulsed, it sends out an ultrasonic wave. When the pulser/receiver 565 generates an electric pulse, it also sends a trigger signal 567 to the DAQ 568 to initiate the DAQ 568 to start the recording. The generated ultrasonic wave propagates within the rock sample 580. Both the incident and reflected ultrasonic waves are picked up by some ultrasonic receivers 545/555. The ultrasonic receivers 545/555 convert the mechanic waves into analog electrical signals. For convenience, the electric signals are termed ultrasonic wave signals. The ultrasonic wave signals transmit from the receivers 545/555 to the DAQ 568 through the bundles of receiving cables 547. The ultrasonic wave signals are digitized by the DAQ 568. The digitized ultrasonic wave signals are sent to the computer 560 to be recorded, as controlled by the application program 561. Each of the transmitters 541 and 551 is fired one by one and the received ultrasonic wave signals are recorded by the computer 560. The next transmitter 541 can be fired when all the ultrasonic wave signals have been collected. The recorded ultrasonic wave signals are processed by the application program 561 to derive some ultrasonic properties of the sample, such as velocity, an ultrasound computer tomography image, or both.

Figure 16:
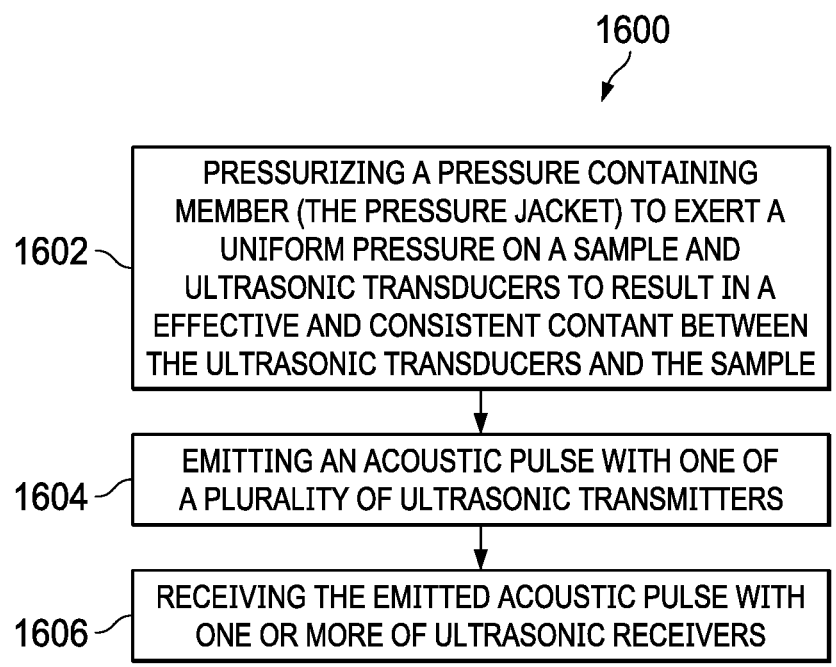
FIG. 16 is a flowchart illustrating an example method that can be used with aspects of this disclosure.

Before loading a sample, the valve 574 is opened. The applied pressure is adjusted gradually to a suitable level to inflate the pressure jacket 530 by adjusting the pressure regulator 573. The valve 574 is then closed to block the pressure connection between the supplied pressurized fluid 570 and the pressure jacket 530. The pressure of the pressure jacket is released gradually by using the bleeding valve 576 to a level such that the center member 51 of the sample chamber 50 can be opened and that the pressure jacket 530 is still in a suitable shape (not completely collapsed). The bleeding valve 576 is then closed to maintain the pressure. The sample chamber 50 is unlocked by releasing one or more lock mechanisms 1910. The sample chamber 50 is opened by laying down the right chamber member 57 and the left chamber member 58 and lifting the upper part of the center chamber member 51. A sample is placed gently on the top of the lower half of the center jacket member 531. The center chamber member 51 is closed, followed by the right chamber member 57 and left chamber member 58. The sample chamber is then securely locked by applying the lock mechanisms 1910. The valve 574 is gradually opened. The applied pressure to the pressure jacket is gradually increased to the required level by adjusting the pressure regulator 573. The applied pressure should be higher than a minimum level to result in a good contact between the transducers and the sample such that the acoustic signals can effectively transmit between the transducers and the sample. Depending on the actual test requirement, a pressure higher than the minimum pressure can be applied. FIG. 16 is a flowchart of an example method 1600 that can be utilized with aspects of this disclosure. At 1602, the pressure jacket is pressurized to exert a uniform pressure on the sample 580 and transducers 544. During operation, a uniform pressure is applied to the center jacket member 531, the right jacket member 537, and the left jacket member 538. The valve 574 is used to close the pressure supply to the pressure jacket. The bleeding valve 576 is used to release the pressure of the pressure jacket when required.

After loading and pressurization, the sample is firmly confined inside the sample chamber under the same confined pressure in all directions. All the transducers 544 are pressed against the sample under the same high pressure. This ensures a consistent, stable, and good contact of the transducers 544 to the sample automatically.

After a sample is loaded, a measurement can be conducted. At 1604, an acoustic pulse is emitted with one of the acoustic transmitters. At 1606, the emitted acoustic pulse is received with one or more of the acoustic receivers. In more detail, as controlled by the application program 561, each of the transmitters 541 and 551 is fired one by one and the ultrasonic wave signals picked up by the receivers 545 and 555 are digitized by the DAQ 568 and the digitized signals are recorded by the computer 560. The next transmitter can be fired when all the ultrasonic wave signals have been collected. The recorded ultrasonic wave signals are processed by the application program 561 to derive some ultrasonic properties of the sample, such as velocity, and ultrasound computer tomography image.

After the testing is completed, the sample 580 can be removed from the sample chamber 50. To start, the valve 574 is closed to block the pressure connection between the supplied pressurized fluid 570 and the pressure jacket 530. The pressure of the pressure jacket is released gradually by using the bleeding valve 576 to a level such that the center member 51 of the sample chamber 50 can be opened and the pressure jacket 530 is still in a suitable shape (not completely collapsed). The bleeding valve 576 is then closed to maintain the pressure. The sample chamber 50 is unlocked by releasing the lock mechanisms 1910. The sample chamber 50 is opened by laying down the right chamber member 57 and the left chamber member 58 and lifting the upper part of the center member 51. The sample 580 can then be removed gently from the sample chamber.

While this specification contains many specific implementation details, these should not be construed as limitations on the scope of what may be claimed, but rather as descriptions of features specific to particular implementations. Certain features that are described in this specification in the context of separate implementations can also be implemented in combination or in a single implementation. Conversely, various features that are described in the context of a single implementation can also be implemented in multiple implementations separately or in any suitable subcombination. Moreover, although features have been previously described as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the implementations previously described should not be understood as requiring such separation in all implementations, and it should be understood that the described components and systems can generally be integrated together in a single product or packaged into multiple products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A testing apparatus comprising:
    a central member defining a sample chamber and comprising an elastic material configured to enclose at least a portion of a sample, a plurality of acoustic receivers configured to detect sound waves in the sample chamber and a plurality of acoustic transmitters configured to emit sounds waves in the central member; and
    a pressure-retaining case surrounding a radial surface of the central member, the pressure-retaining case configured to contain a pressurized fluid between an annulus formed between the pressure-retaining case and the central member, the pressure-retaining case comprising:
        a case central member comprising:
            an upper portion; and
            a lower portion connected to the upper portion along a first edge of the upper portion and a first edge of the lower portion by a hinge, a second edge of the upper portion and a second edge of the lower portion configured to abut one another when the case central member is in a closed position, the upper portion and the lower portion defining a first open end of the pressure-retaining case and a second open end of the pressure-retaining case when in the closed position;
        a right-side member configured to seal the pressure retaining case and the central member, the right-side member configured to seal the first open end of the pressure-retaining case; and
        a left-side member configured to seal the pressure-retaining case and the central member, the left-side member configured to seal the second open end of the pressure-retaining case that is opposite of the first open end of the pressure retaining case.

2. The testing apparatus of claim 1, wherein the acoustic transmitters are ultrasonic emitters and the acoustic receivers are ultrasonic acoustic sensors.

3. The testing apparatus of claim 1, wherein the left-side member and the right-side member are secured with one or more lock mechanisms.

4. The testing apparatus of claim 1, wherein the acoustic receivers and acoustic transmitters are arranged so that one receiver or one transmitter is positioned substantially every 30° around a central longitudinal axis of the sample chamber.

5. The testing apparatus of claim 4, wherein there are two acoustic receivers for every one acoustic transmitters.

6. The testing apparatus of claim 4, wherein the acoustic transmitters and acoustic receivers are arranged in rows transverse to a longitudinal axis of the sample chamber, a composition of each of the rows alternating between two acoustic receivers and one acoustic transmitter.

7. The testing apparatus of claim 1, wherein at least one of the acoustic transmitters is oriented at an angle from an inner surface of the central member.

8. The testing apparatus of claim 1, further comprising a control system comprising:
    a switch coupled to each of the plurality of acoustic transmitters, the switch configured to connect or disconnect a pulser and receiver circuit to a specified acoustic transmitter of the plurality of acoustic transmitters;
    a data acquisition unit coupled to each of the plurality of acoustic receivers, the data acquisition unit configured to receive a signal from each of the plurality of acoustic receivers; and
    the pulser and receiver circuit, wherein the pulse and receiver circuit is coupled to the switch and the data acquisition unit, the pulser and receiver circuit configured to send an electric pulse to one of the plurality of acoustic transmitters through the switch and send a control signal to the data acquisition unit.

9. The testing apparatus of claim 1 further comprising:
a pressure pump coupled to the annulus between the central member and the pressure-retaining case, the pressure pump configured to pressurize the annulus with fluid; and
a pressure sensor coupled to the annulus between the central member and the pressure retaining case, the pressure sensor configured to detect a pressure within the annulus.

10. A method comprising:
pressurizing a pressure containing member to exert a uniform pressure on a sample;
emitting an acoustic pulse with one of a plurality of acoustic emitters; and
receiving the emitted acoustic pulse with one or more of a plurality of acoustic sensors, wherein receiving the emitted acoustic pulse comprises:
receiving a direct incident acoustic pulse through a sample; and
receiving a reflected acoustic pulse through the sample.

11. The method of claim 10, further comprising:
uniformly pressing the plurality of acoustic emitters and the plurality of acoustic sensors against a surface of the sample by an elastic material and the pressure in the pressure containing member.

12. The method of claim 11, further comprising:
depressurizing the pressure containing member; and
releasing the plurality of acoustic emitters and the plurality of acoustic sensors from the surface of the sample in response to depressurizing the pressure containing member.

13. The method of claim 10, further comprising analyzing the received acoustic pulses.

14. The method of claim 13, further comprising determining a rock property based on the received acoustic pulse.

15. The method of claim 14, wherein the determined rock property comprises an acoustic velocity.

16. The method of claim 10, wherein emitting an acoustic pulse comprises:
sending a control signal to a switch from a computer to instruct the switch to make a connection between a pulser and receiver circuit and one of plurality of acoustic emitters; and
sending an electric pulse to a specified acoustic emitter through the switch, from the pulser and receiver circuit, in response to the control signal being received by the switch.

17. The method of claim 10, wherein receiving the emitted acoustic pulse comprises:
sending a control signal to a data acquisition unit from a pulser and receiver circuit; and
receiving a signal by the data acquisition unit from one or more specified acoustic sensors in response to the control signal being received by the data acquisition unit.

18. A system comprising:
a central member defining a sample chamber and comprising an elastic material configured to enclose at least a portion of a sample, a plurality of acoustic sensors configured to detect sound waves in the sample chamber and a plurality of acoustic emitters configured to emit sounds waves in the central member; and
a pressure-retaining case surrounding a radial surface of the central member, the pressure-retaining case configured to contain a pressurized fluid between an annulus formed between the pressure-retaining case and the central member;
a switch coupled to each of the plurality of acoustic emitters, the switch configured to connect or disconnect a pulser and receiver circuit to a specified acoustic emitter of the plurality of acoustic emitters;
a data acquisition unit coupled to each of the plurality of acoustic sensors, the data acquisition unit configured to receive a signal from each of the plurality of acoustic sensors;
the pulser and receiver circuit, wherein the pulser and receiver circuit is coupled to the switch and the data acquisition unit, the pulser and receiver circuit configured to send an electric pulse to one of the plurality of acoustic emitters through the switch and to send a control signal to the data acquisition unit simultaneously;
a pressure pump coupled to the annulus between the central member and the pressure retaining case, the pressure pump configured to pressurize the annulus with fluid; and
a pressure sensor coupled to the annulus between the central member and the pressure-retaining case, the pressure sensor configured to detect a pressure within the annulus.

19. The system of claim 18, wherein the plurality of acoustic sensors and the plurality of acoustic emitters are configured to be transverse to a received sample.

20. The system of claim 18, further comprising a computer readable memory containing instructions comprising:
sending a first control signal to the switch to make a connection between the pulser and receiver circuit and one of the plurality of acoustic emitters;
sending a second control signal to the pulser and receiver circuit to command the pulser and receiver circuit to send an electric pulse to a specified acoustic emitter through the switch and to send a control signal to the data acquisition unit simultaneously in response to the first control signal being received by the switch; and
receiving a signal from one or more specified acoustic sensors through the data acquisition unit in response to the control signal being received by the data acquisition unit.

* * * * *